(12) United States Patent
Dryfe et al.

(10) Patent No.: US 10,415,143 B2
(45) Date of Patent: Sep. 17, 2019

(54) PRODUCTION OF GRAPHENE AND GRAPHANE

(71) Applicant: The University of Manchester, Manchester (GB)

(72) Inventors: Robert Angus William Dryfe, Manchester (GB); Ian Anthony Kinloch, Manchester (GB); Amr M. Abdelkader, Manchester (GB)

(73) Assignee: The University of Manchester, Manchester (GB)

( * ) Notice: Subject to any disclaimer, the term of this patent is extended or adjusted under 35 U.S.C. 154(b) by 379 days.

(21) Appl. No.: 14/907,795

(22) PCT Filed: Aug. 6, 2014

(86) PCT No.: PCT/GB2014/052416
§ 371 (c)(1),
(2) Date: Jan. 26, 2016

(87) PCT Pub. No.: WO2015/019093
PCT Pub. Date: Feb. 12, 2015

(65) Prior Publication Data
US 2016/0168726 A1  Jun. 16, 2016

(30) Foreign Application Priority Data

Aug. 6, 2013 (GB) .................................. 1314084.3

(51) Int. Cl.
*C25B 1/00* (2006.01)
*C01B 32/19* (2017.01)
(Continued)

(52) U.S. Cl.
CPC .............. *C25B 1/00* (2013.01); *C01B 32/182* (2017.08); *C01B 32/19* (2017.08); *C01B 32/20* (2017.08);
(Continued)

(58) Field of Classification Search
CPC ... C07C 13/62; C07C 2603/54; Y02P 20/542; C01P 2004/64; C25B 1/00; C25B 11/12;
(Continued)

(56) References Cited

U.S. PATENT DOCUMENTS 4,486,286 A  12/1984 Lewin et al.
4,608,133 A   8/1986 Morduchowitz et al.
(Continued)

FOREIGN PATENT DOCUMENTS

CN        102465309 A    5/2012
GB           217115 A    6/1924
(Continued)

OTHER PUBLICATIONS

Kakaei et al. (K. Kakaei, M. Zhiani, A new method for manufacturing graphene and electrochemical characterization of graphene-supported Pt nanoparticles in methanol oxidation, J. Power Sources 225 (2013) 356-363; published online Oct. 26, 2012 (Year: 2012)*
(Continued)

*Primary Examiner* — Maris R Kessel
*Assistant Examiner* — Joshua L Allen
(74) *Attorney, Agent, or Firm* — Seed IP Law Group LLP

(57) ABSTRACT

The present invention provides a method for the production in an electrochemical cell of one or more of graphene, graphite nanoplatelet structures having a thickness of less than 100 nm, and graphane, wherein the cell comprises: (a) a negative electrode which is graphitic; (b) a positive electrode which may be graphitic or another material; and (c) an electrolyte selected from (i) an ionic liquid; (ii) a deep eutectic solvent; and (iii) a solid ionic conductor, optionally further comprising (iv) one or more ionic species, wherein the amount of (i), (ii) or (iii) and (iv) is greater than 50 wt % based on the total weight of the electrolyte; and wherein the electrolyte includes a mixture of different cations; and
(Continued)

wherein the method comprises the step of passing a current through the cell to intercalate ions into the graphitic negative electrode so as to exfoliate the graphitic negative electrode.

18 Claims, 10 Drawing Sheets

(51) Int. Cl.
    *C01B 32/20* (2017.01)
    *C07C 13/62* (2006.01)
    *C25B 11/12* (2006.01)
    *C01B 32/182* (2017.01)
    *C01B 32/225* (2017.01)

(52) U.S. Cl.
    CPC ............ *C01B 32/225* (2017.08); *C07C 13/62* (2013.01); *C25B 11/12* (2013.01); *C01B 2204/04* (2013.01); *C01P 2004/64* (2013.01); *C07C 2603/54* (2017.05); *Y02P 20/542* (2015.11)

(58) Field of Classification Search
    CPC ......... C25B 3/04; C01B 32/19; C01B 32/225; C01B 32/20; C01B 32/182; C01B 2204/04; C01B 32/184; B82Y 40/00; B82Y 30/00
    See application file for complete search history.

(56) References Cited

U.S. PATENT DOCUMENTS

| | | | |
|---|---|---|---|
| 5,824,832 A | 10/1998 | Sherif et al. | |
| 7,071,258 B1 | 7/2006 | Jang et al. | |
| 2008/0105561 A1* | 5/2008 | Fray ...................... | B82Y 30/00 205/354 |
| 2008/0206124 A1 | 8/2008 | Jang et al. | |
| 2009/0026086 A1 | 1/2009 | Zhamu et al. | |
| 2009/0090640 A1 | 4/2009 | Jang et al. | |
| 2009/0155578 A1 | 6/2009 | Zhamu et al. | |
| 2009/0169467 A1* | 7/2009 | Zhamu .................. | B82Y 30/00 423/448 |
| 2011/0319554 A1* | 12/2011 | Frazier ................... | B82Y 30/00 524/577 |
| 2012/0321545 A1* | 12/2012 | Jeon ....................... | B82Y 40/00 423/448 |
| 2013/0102084 A1* | 4/2013 | Loh ........................ | B01J 21/185 436/94 |
| 2013/0161199 A1 | 6/2013 | Li et al. | |
| 2013/0164208 A1 | 6/2013 | Hsieh et al. | |
| 2013/0299359 A1* | 11/2013 | Ling ....................... | C25B 31/00 205/412 |
| 2014/0061059 A1 | 3/2014 | Dryfe et al. | |

FOREIGN PATENT DOCUMENTS

| | | |
|---|---|---|
| GB | 1109143 A | 4/1968 |
| JP | 2001-89887 A | 4/2001 |
| JP | 2004-143488 A | 5/2004 |
| WO | 00/64808 A1 | 11/2000 |
| WO | 2006/037955 A1 | 4/2006 |
| WO | 2007/046713 A1 | 4/2007 |
| WO | 2007/093574 A2 | 8/2007 |
| WO | 2008/019154 A2 | 2/2008 |
| WO | 2011/010109 A1 | 1/2011 |
| WO | 2011/111791 A1 | 9/2011 |
| WO | 2011/162727 A1 | 12/2011 |
| WO | 2012/120264 A1 | 9/2012 |
| WO | 2013/132261 A1 | 9/2013 |
| WO | 2014/191765 A1 | 12/2014 |

OTHER PUBLICATIONS

Yang et al. (Z. Yang, Y. Sun, L.B. Alemany, T.N. Narayana, W.E. Billups, Birch reduction of graphite. Edge and interior functionalization by hydrogen, J. Am. Chem. Soc. 134 (2012) 18689-18694; published on Oct. 17, 2012) (Year: 2012).*

Du et al. (C. Du, B. Zhao, X.-B. Chen, N. Birbilis, H. Yang, Effect of water presence on choline chloride-2urea ionic liquid and coating platings from the hydrated ionic liquid, Sci. Rep. 6 (2016) 29225) (Year: 2016).*

Park (B Park, Editors: RE Hester, RM Harrison, (2007). Nanotechnology—Consequences for Human Health and the Environment, p. 11, 1.3.6 Quantum Dots. Royal Society of Chemistry). (Year: 2007).*

Chen et al. (C Chen, L Wang, Y Liu, Z Chen, D Pan, Z Li, Z Jiao, P Hu, C-H Shek, CM Lawrence Wu, JKL Lai, M Wu, Assembling tin dioxide quantum dots to graphene nanosheets by a facile ultrasonic route, Langmuir 29 (2013) 4111-4118). (Year: 2013).*

Low et al. (CTJ Low, FC Walsh, MH Chakrabarti, MA Hashim, MA Hussain, Electrochemical approaches to the production of graphene flakes and their potential applications, Carbon 54 (2013) 1-21) . (Year: 2013).*

Singh et al. (VV Singh, G Gupta, A Batra, NK Nigam, M Boopathi, PK Gutch, BK Tripathi, A Srivastava, M Samuel, GS Agarwal, etc ., Greener electrochemical synthesis of high quality graphene nanosheets directly from pencil and its SPR sensing applications, Adv. Funct. Mater. 22 (2012) 2352-2362). (Year: 2012).*

Abbott et al. (AP Abbott, G Capper, DL Davies, RK Rasheed, V Tambyrajah, Novel solvent properties of choline chloride/urea mixtures, Chem. Commun. (2003) 70-71) (Year: 2003).*

Lu et al. (X Lu, C Zhao, Controlled electrochemical intercalation, exfoliation and in situ nitrogen doping of graphite in nitrate-based protic ionic liquids, Phys. Chem. Chem. Phys. 15 (2013) 20005) (Year: 2013).*

Gu et al. (C Gu, H Zhang, X Wang, J Tu, Synthesis of reduced graphene oxide by an ionothermal method and electrochemical performance, RSC Advances 3 (2013) 11807) (Year: 2013).*

Alanyalioğlu et al., "The synthesis of graphene sheets with controlled thickness and order using surfactant-assisted electrochemical processes," *Carbon* 50:142-152, 2012.

Ang et al., "High-Throughput Synthesis of Graphene by Intercalation-Exfoliation of Graphite Oxide and Study of Ionic Screening in Graphene Transistor," *Journal of the American Chemical Society Nano* 3(11):3587-3594, 2009.

Augustynski et al., "Electroreduction of Carbon Dioxide in Aqueous Solutions at Metal Electrodes," *American Chemical Society, Division of Fuel Chemistry*, pp. 1420-1424, 1996.

Augustynski et al., "Electroreduction of carbon dioxide in aqueous solutions at metal electrodes," *Preprints of Papers, American Chemical Society, Division of Fuel Chemistry*, 1996, retrieved from http://www.osti.gov/scitech/biblio/430375, retrieved on Oct. 23, 2014, 2 pages.

Bae et al., "Roll-to-roll production of 30-inch graphene films for transparent electrodes," *Nature Nanotechnology* 5:574-578, Aug. 2010.

Besenhard et al., "Cathodic reduction of graphite in organic solutions of alkali and $NR_4^+$ salts," *Electroanalytical Chemistry and Interfacial Electrochemistry* 53:329-333, 1974.

Cano-Márquez et al., "Ex-MWNTs: Graphene Sheets and Ribbons Produced by Lithium Intercalation and Exfoliation of Carbon Nanotubes," *Nano Letters* 9(4):1527-1533, 2009.

Choi et al., "Improving the electrochemical properties of graphite/ $LiCoO_2$ cells in ionic liquid-containing electrolytes," *Journal of Power Sources* 195:2368-2371, 2010.

Chung et al., "Origin of Graphite Exfoliation—An Investigation of the Important Role of Solvent Cointercalation," *Journal of the Electrochemical Society* 147(12):4391-4398, 2000.

Deng et al., "The adsorption properties of Pb(II) and Cd(II) on functionalized graphene prepared by electrolysis method," *Journal of Hazardous Materials* 183:923-930, 2010.

DeWulf et al., "Electrochemical and Surface Studies of Carbon Dioxide Reduction to Methane and Ethylene at Copper Electrodes in Aqueous Solutions," *J. Electrochem. Soc.* 136(6):1686-1691, 1989.

(56) References Cited

OTHER PUBLICATIONS

Elias et al., "Control of Graphene's Properties by Reversible Hydrogenation: Evidence for Graphane," *Science* 323:610-613, Jan. 30, 2009. (16 pages).

Ferrari et al., "Raman spectroscopy as a versatile tool for studying the properties of graphene," *Nature Nanotechnology* 8(4):235-246, 2013.

Ferrari et al., "Raman Spectrum of Graphene and Graphene Layers," *Physical Review Letters* 97:187104-1-187104-4, 2006.

Gao et al., "Band Gap Tuning of Hydrogenated Graphene: H Coverage and Configuration Dependence," *The Journal of Physical Chemistry* 115:3236-3242, 2011.

Gao et al., "Electrodeposition of Aluminium from $AlCl_3/Et_3NHCl$ Ionic Liquids," *Acta. Phys.—Chim. Sin.* 24(6):939-944, 2008.

Geim, "Graphene: Status and Prospects" *Science* 324:1530-1534, Jun. 19, 2009.

Geng et al., "Effects of Stage, Intercalant Species and Expansion Technique on Exfoliation of Graphite Intercalation Compound into Graphene Sheets," *Journal of Nanoscience and Nanotechnology* 11:1084-1091, 2011.

Guisinger et al., "Exposure of Epitaxial Graphene on SiC(0001) to Atomic Hydrogen," *Nano Letters* 9(4):1462-1466, 2009.

Hao et al., "Probing Layer Number and Stacking Order of Few-Layer Graphene by Raman Spectroscopy," *Small* 6(2):195-200, 2010.

Hernandez et al., "High-yield production of graphene by liquid-phase exfoliation of graphite," *Nature Nanotechnology* 3:563-568, 2008.

Hsu et al., "Condensed-phase nanotubes," *Nature* 377:687, 1995.

Hsu et al., "Electrolytic formation of carbon nanostructures," *Chemical Physics Letters* 262:161-166, 1996.

Huang et al., "Highly efficient electrolytic exfoliation of graphite into graphene sheets based on Li ions intercalation-expansion-microexplosion mechanism," *Journal of Materials Chemistry* 22:10452-10456, 2012.

Ilyin et al., "Computer simulation and experimental study of graphene-like structures formed by electrolytic hydrogenation," *Physica E: Low-dimensional Systems and Nanostructures* 43:1262-1265, 2011.

Jaiswal et al., "Controlled Hydrogenation of Graphene Sheets and Nanoribbons," *ACS Nano* 5(2):888-896, 2011.

Kakaei et al., "A new method for manufacturing graphene and electrochemical characteristic of graphene-supported Pt nanoparticles in methanol oxidation," *Journal of Power Sources* 225:356-363, 2013.

Kinloch et al., "Electrolytic, TEM and Raman studies on the production of carbon nanotubes in molten NaCl," *Carbon* 41:1127-1141, 2003.

Lee et al., "A graphite foil electrode covered with electrochemically exfoliated graphene nanosheets," *Electrochemistry Communications* 12:1419-1422, 2010.

Li et al., "Processable aqueous dispersions of graphene nanosheets," *Nature Nanotechnology* 3:101-105, 2008.

Liu et al., "Intercalation of Organic Ammonium Ions into Layered Graphite Oxide," *Langmuir* 18:4926-4932, 2002.

Liu et al., "One-Step Ionic-Liquid-Assisted Electrochemical Synthesis of Ionic-Liquid-Functionalized Graphene Sheets Directly from Graphite," *Advanced Functional Materials* 18:1518-1525, 2008.

Lotya et al., "Liquid Phase Production of Graphene by Exfoliation of Graphite in Surfactant/Water Solutions," *Journal of the American Chemical Society* 131:3611-3620, 2009.

Lu et al., "One-Pot Synthesis of Fluorescent Carbon Nanoribbons, Nanoparticles, and Graphene by the Exfoliation of Graphite in Ionic Liquids," *American Chemical Society Nano* 3(8):2367-2375, 2009.

Malard et al., "Raman spectroscopy in graphene," *Physics Reports* 473:51-87, 2009.

Maluangnont et al., "Preparation of a Homologous Series of Graphite Alkylamine Intercalation Compounds Including an Unusual Parallel Bilayer Intercalate Arrangement," *Chemistry of Materials* 23:1091-1095, 2011.

Matis et al., "Surface Doping and Band Gap Tunability in Hydrogenated Graphene," *ACS Nano* 6(1):17-22, 2012.

Matsuo et al., "Electrochemical fluorination of graphite in 47% HF aqueous solution," *Journal of Fluorine Chemistry* 87:145-150, 1998.

Morales et al., "High-quality few layer graphene produced by electrochemical intercalation and microwave-assisted expansion of graphite," *Carbon* 49:2809-2816, 2011.

Novoselov et al., "Electric Field Effect in Atomically Thin Carbon Films," *Science* 306:666-669, 2004.

Otake et al., "$CO_2$ decomposition using electrochemical process in molten salts," *Journal of Physics: Conference Series* 379(1):012038, 2012. (10 pages).

Park et al., "Chemical methods for the production of graphenes," *Nature Nanotechnology* 4:217-224, Apr. 2009.

Poh et al., "High-pressure hydrogenation of graphene: towards graphane," *Nanoscale* 4:7006-7011, 2012.

Ryu et al., "Reversible Basal Plane Hydrogenation of Graphene," *Nano Letters* 8(12):4597-4602, 2008.

Schäfer et al., "On the Way to Graphane—Pronounced Fluorescence of Polyhydrogenated Graphene," *Angewandte Chemi International Edition* 52:754-757, 2013.

Schwandt et al., "The preparation of nano-structured carbon materials by electrolysis of molten lithium chloride at graphite electrodes," *Journal of Electroanalytical Chemistry* 647:150-158, 2010.

Simate et al., "The production of carbon nanotubes from carbon dioxide: challenges and opportunities," *Journal of Natural Gas Chemistry* 19:453-460, 2010.

Simonet et al., "Electrochemical Behaviour of Graphite Cathodes in the Presence of Tetraalkylammonium Cations," *Journal of Electroanalytical Chemistry* 75:719-730, 1977.

Sofo et al., "Graphane: A two-dimensional hydrocarbon," *Physical Review B* 75:153401, 2007. (4 pages).

Su et al., "High-Quality Thin Graphene Films from Fast Electrochemical Exfoliation," *Journal of the American Chemical Society Nano* 5(3):2332-2339, 2011.

Vallés et al., "Solutions of Negatively Charged Graphene Sheets and Ribbons," *Journal of the American Chemical Society* 130:15802-15804, 2008.

Wang et al., "Direct exfoliation of natural graphite into micrometre size few layers of graphene sheets using ionic liquids," *Chemical Communications* 46:4487-4489, 2010.

Wang et al., "Highly efficient and large-scale synthesis of graphene by electrolytic exfoliation," *Carbon* 47:3242-3246, 2009.

Wang et al., "High-Yield Synthesis of Few-Layer Graphene Flakes through Electrochemical Expansion of Graphite in Propylene Carbonate Electrolyte," *Journal of the American Chemical Society* 133:8888-8891, 2011.

Wang et al., "Toward High Throughput Interconvertible Graphane-to-Graphene Growth and Patterning," *ACS Nano* 4(10):6146-6152, 2010.

Yang et al., "Birch Reduction of Graphite. Edge and Interior Functionalization by Hydrogen," *Journal of the American Chemical Society* 134:18689-18694, 2012.

Zbořil et al., "Graphene Fluoride: A Stable Stoichiometric Graphene Derivative and its Chemical Conversion to Graphene," *small* 6(24):2885-2891, 2010.

Zhang et al., "Deep eutectic solvents: syntheses, properties and applications," *Chem. Soc. Rev.* 41:7108-7146, 2012.

Zhang et al., "Physical Properties of Ionic Liquids: Database and Evaluation," *J. Phys. Chem. Ref. Data* 35: 1475-1517, 2006.

Zhong et al., "Enhanced Electrochemical Expansion of Graphite for in Situ Electrochemical Functionalization," *Journal of the American Chemical Society* 134:17896-17899, 2012.

\* cited by examiner

PRODUCTION OF GRAPHENE AND GRAPHANE

FIELD OF INVENTION

The present invention relates to an electrochemical method for the production of graphene (including functionalised graphene and graphene hybrids) and related graphite nanoplatelet structures as well as graphane.

BACKGROUND

Graphene is an atomically thick, two dimensional sheet composed of sp2 carbons in a honeycomb structure. It can be viewed as the building block for all the other graphitic carbon allotropes. Graphite (3-D) is made by stacking several layers on top of each other, with an interlayer spacing of ~3.4 Å and carbon nanotubes (1-D) are a graphene tube. Graphane is hydrogenated graphene, the carbons of the C—H groups being sp3 carbons.

Single-layer graphene is one of the strongest materials ever measured, with a tensile strength of ~130 GPa and possesses a modulus of ~1 TPa. Graphene's theoretical surface area is ~2630 m2/g and the layers are gas impermeable. It has very high thermal (5000+W/mK) and electrical conductivities (up to 6000 S/cm). The observed superior properties of graphene introduced it as a potential candidate material for many applications including but not limited to:

(a) additive for mechanical, electrical, thermal, barrier and fire resistant properties of a polymer;

(b) surface area component of an electrode for applications such as fuel cells, super-capacitors and lithium ion batteries;

(c) conductive, transparent coating for the replacement of indium tin oxide; and (d) components in electronics.

Graphene was first isolated in 2004 by Professor Geim's group. Graphene research since then has increased rapidly. Much of the "graphene" literature is not on true monolayer graphene but rather two closely related structures:

(i) "few layer graphene", which is typically 2 to 10 graphene layers thick. The unique properties of graphene are lost as more layers are added to the monolayer and at 10 layers the material becomes effectively bulk graphite; and (ii) Graphene oxide (GO), which is a graphene layer which has been heavily oxidised in the exfoliation process used to make it and has typically 30 at % oxygen content. This material has inferior mechanical properties, poor electrical conductivity and is hydrophilic (hence a poor water barrier).

There are a variety of methods to produce graphene [Ruoff 2009]. Novoselov et al. produced their first flakes by the mechanical exfoliation of graphite by using an adhesive tape to isolate individual layers [Novoselov 2004]. It has been shown subsequently that graphite can also be exfoliated by using ultrasonic energy to separate the layers when in an appropriate solvent, such as NMP (N-methyl pyrrolidone) [Coleman 2008 & 2009].

Graphite is an allotrope of carbon, the structure of which consists of graphene layers stacked along the c-axis in a staggered array usually denoted as ABAB. The layers are held together by weak van der Waals forces so that the separation between layers is 0.335 nm. Graphite is a cheap and abundant natural material, which makes it an excellent raw material for inexpensive production of graphene.

As noted above, graphite has been used to make graphene via exfoliation, wherein the stacked layers of graphite are separated to produce graphene. This has been achieved by using ultrasound (ultrasonic exfoliation, USE) and also by intercalating compounds into the graphite interlayer structure so as to weaken the interlayer bonding and promote layer separation.

There are two routes that have been reported to intercalate compounds into graphite structure: chemical and electrochemical. The chemical method is based on the direct reaction of solid graphite materials with the intercalation species (usually in liquid or vapour phase). This process is kinetically slow and usually assisted by sonication or heating. The second route, the electrochemical approach, involves generating the intercalated species through an electrochemical reaction on a graphite cathode or on a graphite anode.

The most famous example of the electrochemical approach is based on the lithium ion battery. For decades, graphite was used as negative electrode in lithium ion battery due to its high electrical conductivity and its ability to host lithium between the graphene layers. The lithium-graphite intercalation compounds decompose readily in water giving rise to lithium hydroxide and free standing graphene sheets. Loh et al. mimicked the lithium ion battery principle to intercalate Li into graphite and then applied a sonication step to exfoliate graphite [US 2013/0102084 A1, and WO 2011/162727]. This work is also discussed in a related paper [Wang 2011]. However, due to the slow kinetic nature of the intercalation process, the lithium was limited to the areas close to the edges. Upon exfoliation in water, graphite with expanded edges was produced and further intercalation, water decomposition and sonication steeps were needed to achieve exfoliation.

Liu et al. [Liu 2008] reported the exfoliation of graphite using an ionic liquid-water mixture electrolyte to form "kind of IL-functionalized" graphene nanosheets. Scheme 1 in this paper suggests that the material was produced by the exfoliation of the anode but in their discussion the authors mention the role of the cation. Lu subsequently studied the route in more detail and discussed the possible mechanism involved in the production process [Lu 2009]. In their paper, they stated "according to the proposed mechanism by Liu, the positively charged imidazolium ion is reduced at the cathode to form the imidazolium free radical which can insert into the bonds of the graphene plane. At the fundamental level, there are several questionable aspects about the radical-insertion mechanism proposed by Liu, especially when the ILs are mixed with water at 1:1 ratio and where an operational voltage as high as 15 V is applied". Lu et al. showed that the graphene nanosheet production is exclusively at the anode and is due to an interaction of decomposed water species and the anions from the ionic liquid, such as $BF_4^-$.

The present inventors reported in WO2012120264-A1 the exfoliation of graphite through the electrochemical ammonia-graphite intercalated compound. Without sonication or repeating the intercalation/decomposition steps, the product was few layer graphene with a particle size in the submicron level. Swager and Zhong [Zhong 2012] proposed a method to intercalate graphite with Li and then with ammonia in two separate steps. However, due to the expanding nature of the cathode, the electrodes distance was initially large and hence high voltage was applied to overcome the high internal resistance (IR) drop. As a result, the organic solvent used as electrolyte dissociated at later stages of the process and hindered the intercalation process. Therefore, an additional sonication step was necessary to achieve reasonable exfoliation.

Huang et al [Huang 2012] have used molten LiOH at 600° C. to generate intercalated $Li_xC_y$ species via an in-situ reduction process. Huang reports that it is the reduced $Li_xC_y$ species (and not the Li ions) that causes the desired expansion of the graphite. The expanded graphite is subsequently exfoliated in a distinct, separate aqueous sonication step.

For completeness it is noted that under the right conditions the fragments from the disintegrated negative electrode can be nanoscale forms of a carbon. The production of carbon nanotubes from the intercalation of alkali metal ions into a graphite cathode has been reported by Hsu et at [Hsu 1995], and Kinloch et al. [Kinloch 2003]. These nanotubes were produced using a molten alkali halide electrolyte at high temperatures (600° C. or higher). In addition to carbon nanotubes, graphite platelets, carbon nanoparticles and amorphous structures were observed. However, no graphene was reported.

As is clear from the discussion above, a disadvantage of reported methods is that they produce a mixture of materials dispersed in solution (centrifugation is needed for separation). Furthermore, desirable yields of monolayer samples can only be achieved with prolonged application of ultrasonic exfoliation (USE) meaning that the lateral flake dimensions are very small (<1 micron), thus precluding many applications in electronic devices. Furthermore, the large-scale use of power ultrasound has raised safety concerns amongst industrial parties.

Another electrochemical method has been introduced whereby double intercalation of graphite occurs with metal and organic ions. This method does not use any sonication, but it can suffer from decomposition of the organic solvent depending on the conditions used [co-pending unpublished application PCT/GB2013/050573].

Intercalation compounds can also be produced by introducing a metal through the vapour phase and then reacting these ions. The layers of the intercalation compound can then be separated by stirring in an appropriate solvent, such as NMP [Valles 2008]. An intercalation approach has also been taken to separate graphene oxide aggregates by electrostatically attracting tetrabutylammonium cations in between the layers of the graphene oxide [Ang 2009]. This technique relies on the charges present in graphene oxide to attract the tetrabutylammonium cations.

Wang et al. have shown that ionic liquids are also appropriate solvents for ultrasonic exfoliation because of their stabilising effect on the resultant graphene. In this case, they mixed graphite powder with ionic liquids such as 1-butyl-3-methyl-imidazolium bis(trifluoromethanesulfonyl)imide ([Bmim][Tf$_2$N]) and then subjected the mixture to tip ultrasonication for a total of 60 minutes using 5-10 minute cycles. The resultant mixture was then centrifuged [Wang 2010].

Graphene can also be produced by chemical vapour deposition. For example, methane can be passed over copper [Bae 2010]. Similar methods are also used to form carbon nanotubes [Simate 2010]. However, these methods are typically procedurally complex, require extremely high temperatures (e.g. up to 1000° C.) and usually require elaborate isolation techniques to obtain the material formed.

Alternatively silicon carbide can be decomposed to make a graphene film.

The present application is also concerned with the production of graphane. For certain applications graphane has more favourable electronic properties than graphene. Graphene exhibits an ambipolar electric field effect, ballistic conduction of charge carriers, and the quantum Hall effect at room temperature [Geim 2009]. However, graphene has a major drawback when it comes to applications in electronics. Graphene represents a nearly ideal two-dimensional conductor, making it hard to create graphene-based transistors that are suitable for integrated circuits where semiconductors with controllable band gaps are required. Hydrogenation transforms the hybridization of carbon atoms from sp2 into sp3, resulting in removing the conducting $\pi$-bands and opening an energy gap. The C/H ratio and the distribution and ordering of H atoms play a crucial role on tuning the conductivity [Matis 2011; Jaiswal 2011; Gao 2011].

Graphane (CH)n, the fully hydrogenated analogue of graphene, was theoretically predicted by Sofo et al [Sofo 2007]. They proposed two favourable conformations of graphane: (1) boat conformer where the hydrogen atoms alternate in pairs, and (2) chair conformer with the hydrogen atoms alternating on both sides of the carbon plane. They also suggested a number of routes to synthesize graphane including substituting fluorine in fluorinated graphene with hydrogen by exchange with sodium hydride, or starting from graphite and using a Birch-type reaction. However, graphene hydrogenation by cold plasma was the first technique used to isolated graphane sheet experimentally [Elias 2009]. A number of other approaches have then been suggested including: electron-induced dissociation of hydrogen silsesquioxane [Ryu 2008], exposed epitaxial graphene on SiC to atomic hydrogen [Guisinger 2009], plasma-enhanced chemical vapor deposition [Wang 2010], and thermal exfoliation of graphite oxide in a hydrogen atmosphere under high pressure [Poh 2012].

The above-mentioned methods suffer from the limited yield and/or high production cost of the graphane materials. Wet chemical approaches may represent a cheap alternative for mass production, which motivated many researchers to recall Sofo's suggestion of using reducing agent with graphite in liquid ammonia. This type of chemical reaction, known as Birch reduction, is widely used for hydrogenation of polyaromatic hydrocarbons. It has been also used to hydrogenate buckminsterfullerene, fullerenes, carbon nanotubes, charcoal, and coals. Recently, Birch reduction was used to functionalise graphene using lithium in liquid ammonia and tert-butyl alcohol [Yang 2012] or water/ethanol mixture [Schäfer 2013] as a proton sources. Naturally, there are difficulties, and high costs, associated with handling liquid ammonia and reactive metals.

As is clear from the above comments, further methods for the production of graphene/graphite nanoplatelet structures/graphane are desired so as to mitigate or obviate the problems identified above. In particular, methods that produce graphene sheets with a controlled number of layers and flake size, and also more accessible methods for producing graphane.

Advantageously, the methods should be scalable to allow for the production of graphene on a large scale. For instance, there is a desire to provide new methods that produce graphene/graphite nanoplatelet structures/graphane selectively over other carbon allotropes, which are amenable to scale-up to an industrial platform, which are more efficient, reliable, environmentally friendly, provide higher quality material, provide increased yields of material, provide larger sheets or material, provide easier isolation of material and/or which are procedurally simpler and/or cheaper than the methods of the prior art.

DESCRIPTION OF THE INVENTION

At its most general the present disclosure proposes that exfoliation by ion intercalation should be carried out in an electrochemical cell not with the aqueous or organic solvent-based electrolyte solutions discussed above but instead with electrolytes having a very substantial concentration of ionic species, suitably an ionic liquid, deep eutectic solvent or a solid ionic conductor, and a low concentration of, suitably no, conventional solvent (i.e. water and organic solvents). The present inventors have found that using high ion concentration electrolytes with a low concentration of, or no, conventional solvents allows the electrodes to be widely separated without a high internal resistance (IR) drop. In turn this means that a lower potential is required, which mitigates or eliminates the problem of uncontrolled decomposition of certain electrolyte components. Furthermore the lower IR drop means less energy loss in the cell, reducing the cost of the process. These advantages are achieved whilst still maintaining the excellent exfoliation performance observed using conventional salt solutions in aqueous or organic solvents.

The present inventors have found that in the context of the electrochemical production of graphene from a negative graphitic electrode (i.e. production of graphene from graphite via a cathodic process), the use of these high ion concentration electrolyte(s) is important as it allows the large expansion of the graphite cathode associated with high levels of ion intercalation and the subsequent exfoliation of the graphene layers. Also, the high ion concentration electrolyte has the advantages of non-flammability, possessing a high thermal stability, having a negligible vapor pressure and being easily recyclable. These factors reduce or eliminate the safety problems associated with the organic solvents and also provide an eco-friendly process, whilst still providing excellent intercalation and exfoliation performance.

The high ion concentration electrolytes can be provided by three related types of electrolyte: (i) ionic liquids (also known as molten salts); (ii) deep eutectic solvents (DES); and (iii) solid ionic conductors. All three of these electrolytes are characterised not only in that they comprise high ion concentrations but also in that they are either devoid of non-ionic species or the non-ionic species are not conventional (aqueous or organic) solvents and instead form part of the matrix of the electrolyte to facilitate movement of ions within the electrolyte (for example, some deep eutectic solvents contain as part of the eutectic mixture a non-ionic hydrogen bond donor).

Thus, ionic liquids comprise salts ($X^+Y^-$); deep eutectic solvents comprise salts ($X^+Y^-$) and in some cases a non-ionic species (Z) that, together with the salt, reduces or suppresses the melting point of the salt such that the deep eutectic solvent ($X^+Y^-Z$) has a lower melting point than the pure salt or the melting point reducing/suppressing component; and a solid ionic conductor comprises salts ($X^+Y^-$). By using these related electrolytes rather than conventional solvent-based electrolytes, the present inventors have accessed a more efficient, cleaner and safer electrochemical route to graphene and related structures as well as a greater range of in-situ functionalization options.

In a first aspect the present invention provides a method for the production in an electrochemical cell of one or more of graphene, graphite nanoplatelet structures having a thickness of less than 100 nm, and graphane, wherein the cell comprises:

(a) a negative electrode which is graphitic;
(b) a positive electrode which may be graphitic or another material; and
(c) an electrolyte suitably comprising more than 50 wt %, based on total weight of the electrolyte, of ionic species, suitably an electrolyte selected from (i) an ionic liquid; (ii) a deep eutectic solvent; and (iii) a solid ionic conductor, optionally further comprising (iv) one or more ionic species, wherein the amount of (i), (ii) or (iii) and (iv) is greater than 50 wt % based on the total weight of the electrolyte;

and wherein the method comprises the step of passing a current through the cell to intercalate ions into the graphitic negative electrode so as to exfoliate the graphitic negative electrode.

Thus, the present disclosure provides a convenient, low energy one-step/one-pot process for obtaining graphene and related materials. In particular, this is achieved without significant loss of the electrolyte because it can be recovered/recycled/reused. This is a significant technical improvement as compared to the use of conventional solvent-based electrolytes. The use of high ion concentration electrolytes with low levels of, or no, conventional solvents means that the cathodic processes at the graphitic negative electrode can proceed cleanly without interference from solvent breakdown products. A further advantage is that a very significant proportion of the graphitic negative electrode can be converted to the desired product because (a) there is little or no interference from undesirable breakdown products; and (b) a large electrode separation can be used because of the good conductivity (low internal resistance, IR) of the electrolyte of the present disclosure.

A yet further advantage of the present disclosure is that the graphene and graphene-related products of the method may be more amenable to biological applications (for example medical applications) because of the low levels or absence of conventional organic solvents. In this connection, "cleaning" or working-up of the products is less onerous because of the comparatively clean method of formation.

In contrast to the method of Huang referred to above, the method of the present disclosure does not necessarily need high temperature or sonication to achieve exfoliation. Furthermore, significant expansion of the graphite and the breaking apart of the graphitic layers is achieved by ion intercalation without the need for subsequent reduction/reaction of intercalated ions.

A yet further advantage of the present disclosure is that a wider potential window can be accessed, because of the characteristics of the electrolyte, meaning that there are more possibilities to access interesting and varied chemistry at the graphitic negative electrode. For example, this may permit functionalisation of the graphene, graphite nanoplate structures and graphane in the cell.

Indeed, as is described in more detail below, the present disclosure provides a one-step method of producing graphane from graphite. The examples herein mimic the Birch reduction by in-situ generation of lithium and ammonium derivatives locally on the surface of a graphite cathode. This eliminates the problems associated with handling and purifying liquid ammonia and reactive metals. The electrochemical reaction is superior to the slow chemical reaction that usually takes several days to produce reasonable yield.

Another advantage arising from the flexibility of the method of the present disclosure is that metal-containing materials can be formed, in the electrochemical cell, on the graphene and graphene related materials. This opens up the possibility of producing "hybrid" materials in which graphene/graphite nanoplatelet structures/graphane can be produced (and suitably isolated) with metal-containing nanoparticles on at least some of the graphene/graphane surfaces. These hybrid materials have potentially wide-ranging applications.

In embodiments, the electrolyte of the present disclosure, particularly ionic liquids and deep eutectic solvents, can be handled and processed more easily, and at lower cost, than conventional solvent-based electrolytes. This is a valuable advantage when considering scale-up of the process.

Thus, in recognising and demonstrating that, contrary to the teaching and clear direction of the prior art, the "solvent free" electrolyte of the present disclosure when used in the context of the cathodic intercalation of ions and in-situ exfoliation, the present inventors have made a valuable contribution to the art.

In embodiments the production of graphene, related graphite nanoplatelet structures, and graphane by exfoliation is driven by the electrochemical insertion of both positive organic ions (e.g. alkylammonium ions) and positive metal ions (e.g. iron, tin, lithium ions) into a negative graphitic electrode. Without wishing to be bound by theory, it is thought that by using cations to exfoliate the negative electrode, the possibility of the formation of graphene oxide through oxidative attack is reduced. This insertion of both organic and metal cations in the same process and in the context of the specific type of electrolyte described herein provides a clean and efficient process for the production of graphene and graphene-type materials.

Graphene, Graphite Nanoplatelet Structures and Graphane

In the present application, the term "graphene" is used to describe materials consisting of ideally one to ten graphene layers, preferably where the distribution of the number of layers in the product is controlled. Similarly, the term "graphane" is used to describe materials consisting of ideally one to ten graphane layers, preferably where the distribution of the number of layers in the product is controlled. The method can also be used to make graphite nanoplatelet structures under 100 nm in thickness, more preferably under 50 nm in thickness, more preferably under 20 nm in thickness, and more preferably under 10 nm in thickness. The size of the graphene or graphane flakes produced can vary from nanometres across to millimeters, depending on the morphology desired.

In embodiments, the material produced is graphene having up to ten layers. The graphene produced may have one, two, three, four, five, six, seven, eight, nine or ten layers. It may be preferred that the material produced is substantially free of graphene oxide. "Substantially free" means less than 10% by weight, preferably less than 5% by weight, more preferably less than 1% by weight of graphene oxide. Additionally or alternatively, preferably the material produced is substantially free of oxygen-containing functional groups. "Substantially free" in the context of oxygen-containing groups means less than 20 at % (atomic percentage) oxygen in the material based on the total number of atoms in the material, preferably less than 10 at %, more preferably less than 6%, and most preferably about the same at % as the graphitic starting material.

In embodiments, the material produced may comprise at least 10% by weight of graphene having up to ten layers, preferably at least 25% by weight and more preferably at least 50% by weight of graphene having up to ten layers.

In embodiments, the material produced is graphane having up to ten layers. The graphane produced may have one, two, three, four, five, six, seven, eight, nine or ten layers. It may be preferred that the material produced is substantially free of graphene oxide. "Substantially free" means less than 10% by weight, preferably less than 5% by weight, more preferably less than 1% by weight of graphene oxide. Additionally or alternatively, preferably the graphane produced is substantially free of oxygen-containing functional groups. "Substantially free" in the context of oxygen-containing groups means less than 20 at % (atomic percentage) oxygen in the material based on the total number of atoms in the material, preferably less than 10 at %, more preferably less than 6%, and most preferably about the same at % as the graphitic starting material.

In embodiments, the material produced may comprise at least 10% by weight of graphane having up to ten layers, preferably at least 25% by weight and more preferably at least 50% by weight of graphane having up to ten layers.

The process of the present invention produces graphene and/or graphite nanoplatelet structures having a thickness of less than 100 nm and/or graphane. In embodiments, the process produces graphene or graphite nanoplatelet structures having a thickness of less than 100 nm or graphane. In embodiments, the process produces graphene and graphite nanoplatelet structures having a thickness of less than 100 nm. In embodiments, the process of the present invention produces graphene. In embodiments, the process produces graphite nanoplatelet structures having a thickness of less than 100 nm. In embodiments the process produces graphane. The process of the present invention may for example produce graphene or a combination of graphene and graphite nanoplatelet structures having a thickness of less than 100 nm. The process of the present invention may for example produce graphane or a combination of graphane and graphene, or a combination of graphane and graphite nanoplatelet structures having a thickness of less than 100 nm.

In embodiments, the process produces more graphene by surface area than graphite nanoplatelet structures having a thickness of less than 100 nm, preferably wherein substantially all material produced by the process is graphene by surface area (wherein at least 90%, preferably at least 95%, more preferably at least 98%, e.g. at least 99% of the material produced by the process is graphene by surface area), such as wherein all material produced by the process is graphene. In embodiments, the process produces more graphene by weight than graphite nanoplatelet structures having a thickness of less than 100 nm, preferably wherein substantially all material produced by the process is graphene by weight (wherein at least 90%, preferably at least 95%, more preferably at least 98%, e.g. at least 99% of the material produced by the process is graphene by weight), such as wherein all material produced by the process is graphene. Thus, in some embodiments, the graphene consists of one to five graphene layers, preferably one to four graphene layers, more preferably one to three graphene layers, for instance one to two graphene layers, e.g. one layer. The graphene produced may therefore have one, two, three, four, five, six, seven, eight, nine or ten layers.

The graphene and/or graphite nanoplatelet structures produced by the present process may contain one or more functionalised regions. "Functionalised" and "functionalisation" in this context refers to the covalent bonding of an atom to the surface of graphene and/or graphite nanoplatelet structures, such as the bonding of one or more hydrogen atoms (such as in graphene) or one or more oxygen atoms (such as in graphene oxide) or one or more oxygen-containing groups, etc. Typically, the material produced by the present process is substantially free of functionalisation, for instance, wherein less than 10% by weight, such as less than 5% by weight, preferably less than 2% by weight, more preferably less than 1% by weight of the relevant product is functionalised. Additionally or alternatively the material produced by the present process contains less than 10 at % total non-carbon elements (for example, oxygen and/or hydrogen) based on the total number of atoms in the material, such as less than 5 at %, preferably less than 2 at %, more preferably less than 1 at %.

For instance, in the above aspect and embodiments it may be preferred that the material produced is substantially free of graphene oxide (i.e. wherein less than 10% by weight, such as less than 5% by weight, preferably less than 2%, more preferably less than 1% by weight of the material produced is graphene oxide). Alternatively or additionally it may be preferred that the material produced is substantially free of oxygen-containing groups such that the material contains less than 20 at % (atomic percentage) oxygen in the material based on the total number of atoms in the material, preferably less than 10 at %, more preferably less than 6%, and more preferably about the same, or less, at % as the graphitic starting material. In embodiments, the material contains less than 5 at %, preferably less than 2 at %, preferably less than 1 at % and most preferably less than 0.5 at % oxygen in the material.

The functionalisation, where present, may occur on the material surface and/or near or at the grain boundary. Typically, the functionalisation, where present, occurs at the grain boundary but not on the material surface. In preferred embodiments, the graphene produced by the present process is not functionalised.

In other embodiments, it may be desirable to have higher levels of functionalisation. For example, the method may include functionalising the material in the cell. Indeed, as noted above, an advantage of the present invention is that it provides increased flexibility for in-situ functionalisation of the material in the cell. Thus, in embodiments, the graphene and/or graphite nanoplatelet structures produced by the present process contain one or more functionalised regions such that more than 10% by weight, suitably more than 15% by weight, suitably more than 20% by weight, suitably more than 30% by weight, suitably more than 40% by weight, of the relevant product is functionalised. Additionally or alternatively the material produced by the present process contains more than 5 at % total non-carbon elements (for example, oxygen and/or hydrogen) based on the total number of atoms in the material, suitably more than 10 at %, preferably more than 15 at %, preferably more than 20 at %, and more preferably more than 30 at %. The functionalised regions may for example comprise oxygen-containing groups covalently bonded to the carbon, or hydrogen bonded to the carbon. Thus, in embodiments, the material can be functionalised with hydrogen to produce a material having an extent of hydrogenation that lies between graphene and graphane. In this way, the properties of the material can be tailored.

In the case of graphane (already "functionalised" with hydrogen atoms) it is preferred that the material produced by the present process is substantially free of further functionalization (i.e. functionalization other than hydrogen atoms), for instance, wherein less than 10% by weight, such as less than 5% by weight, preferably less than 2% by weight, more preferably less than 1% by weight of the relevant product is functionalised. Additionally or alternatively the material produced by the present process contains less than 10 at % total non-carbon elements (for example, oxygen and/or hydrogen) based on the total number of atoms in the material, such as less than 5 at %, preferably less than 2 at %, more preferably less than 1 at %. In preferred embodiments, the graphane produced by the present process is not functionalised.

In other embodiments, graphane includes functionalised regions (i.e. regions where the C—H bonding is replaced such that different atoms, for example oxygen or an oxygen-containing group are covalently bonded to the material). Suitably the graphane produced by the present process contain one or more functionalised regions such that more than 10% by weight, suitably more than 15% by weight, suitably more than 20% by weight, suitably more than 30% by weight, suitably more than 40% by weight, of the graphane is functionalised. Additionally or alternatively the material produced by the present process contains more than 5 at % total non-carbon and non-hydrogen elements (for example, oxygen) based on the total number of atoms in the material, suitably more than 10 at %, preferably more than 15 at %, preferably more than 20 at %, and more preferably more than 30 at %.

The atomic composition of material produced by the present process may be quantified by X-ray photoelectron spectroscopy (XPS). Raman spectroscopy (as described in the Examples) may be used to determine the level of defects in the material.

In embodiments, the material produced by the present process includes at least 10% by weight of graphene having up to ten layers, preferably at least 25% by weight more preferably at least 50% by weight of graphene having up to ten layers, preferably at least 60% by weight, at least 70% by weight, at least 80% by weight, at least 90% by weight, at least 95% by weight, at least 98% by weight, more preferably at least 99% by weight. In embodiments, graphene is produced in the absence of graphite nanoplatelet structures.

The graphite nanoplatelet structures have a thickness of less than 100 nm. In embodiments, the graphite nanoplatelet structures are ≤90 nm thick, such as ≤80, ≤70, ≤60, ≤50, ≤40, ≤30 or ≤20 nm thick, preferably ≤10 nm thick and more preferably ≤1 nm thick.

In embodiments, the material produced by the present process includes at least 10% by weight of graphane having up to ten layers, preferably at least 25% by weight more preferably at least 50% by weight of graphane having up to ten layers, preferably at least 60% by weight, at least 70% by weight, at least 80% by weight, at least 90% by weight, at least 95% by weight, at least 98% by weight, more preferably at least 99% by weight. In embodiments, graphane is produced in the absence of graphene and graphite nanoplatelet structures.

Typically, the process of the present invention produces flakes of graphene or graphane on the electrode and/or in the electrolyte. The size of the graphene flakes produced can vary from nanometres across to millimeters, depending on the morphology desired. The flakes produced are desirably at least 90 µm in length, such as at least 80 µm, 70 µm, 60 µm, 50 µm, 40 µm, 30 µm, 20 µm, 10 µm, or 5 µm, for example at least 1 µm. In embodiments, the flakes produced are 1 to 100 µm in length, such as 1 to 90 µm, 1 to 80 µm, 1 to 70 µm, 1 to 60 µm, 1 to 50 µm, 1 to 40 µm, 1 to 30 µm, 1 to 20 µm, 1 to 10 µm, or 1 to 5 µm in length.

Graphene, Graphite Nanoplatelet Structures and Graphane Hybrids

The method of the present invention is flexible in that it provides for the possibility of introducing, in the electrochemical cell, nanoscale materials onto the surface of the graphene/graphite nanoplatelet structures/graphane. In particular, suitably the graphene/graphite nanoplatelet structures/graphane produced by the method comprises on at least some of the surface a metal-containing material. The present inventors believe that the metal-containing materials do not covalently bond to the surface and instead there is a more general association/affinity between the metal-containing materials and the graphene/graphite nanoplatelet structures/graphane surface. Thus, these "hybrid" materials can still be regarded as graphene/graphite nanoplatelet structures/graphane, albeit with metal-containing materials located on their surface.

Suitably the metal-containing material is in the form of nanoparticles, suitably having a mean average diameter (as measured by TEM) in the range less than 50 nm, preferably less than 25 nm, more preferably less than 20 nm, and more preferably less than 15 nm.

In embodiments the metal-containing materials are metal. The nanoparticles on the surface of the graphene/graphite nanoplatelet structures/graphane are therefore preferably metal nanoparticles. Preferred metals are Fe and Sn. Sn is particularly preferred. Suitably the metal in the metal-containing material is derived from an ionic species in the electrolyte. For example, it can be derived from component (iv) of the electrolyte, suitably a salt, suitably a metal halide, preferably a metal chloride.

Suitably the "surface density" of the metal-containing particles (as measured by TEM) is at least 10 particles/$10^4$ $nm^2$, preferably at least 20 particles/$10^4$ $nm^2$.

Suitably the majority (more than 50%, preferably more than 75%, preferably more than 90%, preferably more than 95%) of the surface area of the graphene/graphite nanoplatelet structures/graphane comprises metal-containing material.

Examples of these "hybrid" materials are disclosed in Examples 7, 8 and 9 (see FIGS. 10, 11, 12A and 12B).

Negative Electrode

The negative electrode is the electrode held at the more negative potential out of the negative and positive electrodes. An additional reference electrode may also be used (which may be any suitable material, such as Ag/AgBF$_4$).

The negative electrode may comprise a layered graphite compound in which cations can be intercalated. Preferred materials include highly ordered pyrolytic graphite (HOPG), natural and synthetic graphite. The electrode may be a single graphitic crystalline flake or many flakes held together. In the latter case, the crystals may be placed on a conductive surface, physically pressed together or held together using a binder such a pyrolysed polymer (e.g. an extruded graphite rod). They also may be held together in a porous box or basket. The minimum lateral dimensions of the graphite flakes are preferably at least 1 nm, more preferably at least 100 nm and most preferably at least 1 micron. The maximum lateral dimensions of the graphite flakes are preferably no more than 10 cm, more preferably no more than 1 mm and most preferably no more than 100 microns. In one embodiment, the flakes are orientated so that the [002] direction is parallel to the surface of the electrode, exposing the galleries for intercalation. In further embodiments, the maximum lateral dimensions of the graphite flakes are preferably no more than 1 micron or 10 microns.

The negative electrode material may be treated prior to use in order to improve its electrochemical exfoliation. In one embodiment the electrode is made from material which has been previously partially exfoliated using other methods such gaseous expansion or intercalation from the vapour phase. For example, commercially available material from companies such as XG Sciences and Angstrom could be used for the electrode material.

In some embodiments, the negative electrode may be of a ladle design to avoid issues with disintegration of the electrode into large pieces. In other embodiment, the graphite negative electrode may be held at a liquid-liquid interface. In such an embodiment, the negative electrode may be a liquid metal such as mercury or gallium on which graphite flakes are placed, allowing continual contact with the graphitic material as it is exfoliated into the desired material.

In some embodiments, the negative electrode may be surrounded by a membrane. Without wishing to be bound by theory, the use of a membrane may help retain any exfoliated material in electrical contact with the negative electrode allowing for further intercalation of the cations. In some embodiments, the pore size of the membrane may vary from 10 nm to 500 nm. Suitable membranes include (a) cellulose dialysis membrane (e.g., Spectra Por 7, 25 nm pores); and (b) polycarbonate membranes (e.g. 450 nm pores) and (c) muslin cloth.

The negative electrode may be provided with a gas, or a gas supply means may be associated with the electrode, for the purpose of increasing the concentration of gas at the electrode. For example, the gas can be hydrogen so as to promote hydrogenation at the electrode. The gas may be supplied by bubbling the gas into/through the electrolyte surrounding the electrode.

Positive Electrode

The positive electrode is the electrode held at the more positive potential of the negative and positive two electrodes.

The positive electrode may consist of any suitable material known to those skilled in the art as it does not play a role in the graphene/graphane production, other than to provide a counter electrode for the anions. Preferably, the positive electrode is made from an inert material such as gold, platinum or carbon. In further embodiments, the positive electrode may be made of a material that oxidises to give the metal ions in the electrolyte, such as lithium.

When the reaction at the positive electrode generates a gas the electrode surface area is as large as possible to prevent gas bubbles wetting it and/or disrupting the process at the negative electrode. The positive and/or reference electrode may also be placed in a membrane or molecule sieve to prevent undesired reactions in the electrolyte or at either electrode. The positive and the negative electrodes could alternatively be placed in a two-compartment cell, wherein the each compartments contains one electrode, and the compartments are connected through a channel.

Electrolyte

The electrochemical cell comprises an electrolyte comprising more than 50 wt % ionic species, based on the total weight of the electrolyte, suitably an electrolyte selected from (i) an ionic liquid; (ii) a deep eutectic solvent; and (iii) a solid ionic conductor, optionally further comprising (iv) one or more ionic species, wherein the amount of (i), (ii) or (iii) and (iv) in the electrolyte is greater than 50 wt % based on the total weight of the electrolyte.

Suitably the electrolyte includes a mixture of different cations, for example two or more different cations. In embodiments, the electrolyte comprises a metal cation and an organic cation.

Thus, the electrolyte is provided by an ionic liquid, a deep eutectic solvent (DES), or a solid ionic conductor, optionally with added ionic species such as salts. In each case the ionic liquid/DES/solid ionic conductor can be a single ionic liquid/DES/solid ionic conductor or a mixture.

In embodiments, the electrolyte comprises, preferably consists essentially of, preferably consists of, (i) and optionally (iv).

In embodiments, the electrolyte comprises, preferably consists essentially of, preferably consists of, (ii) and optionally (iv).

In embodiments, the electrolyte comprises, preferably consists essentially of, preferably consists of, (iii) and optionally (iv).

Ionic liquids and deep eutectic solvents are preferred, with deep eutectic solvents particularly preferred.

The electrolyte of the present disclosure is therefore different from conventional aqueous or organic solvent-based electrolytes wherein a salt (ionic species) is dissolved in a bulk solvent (non-ionic species).

Thus, the electrolyte of the present disclosure can be said to be an ionic electrolyte or ionic solvent (in contrast to conventional solvent systems where the solvent, for example water or an organic solvent, is non-ionic).

In embodiments the amount of ionic species is greater than 55 wt % based on the total weight of the electrolyte, preferably greater than 60 wt %, preferably greater that 65 wt %, preferably greater than 70 wt %, preferably greater than 75 wt %, preferably greater than 80 wt %, preferably greater than 85 wt %, preferably greater than 90 wt %, more preferably greater than 95 wt %, more preferably greater than 97 wt %, more preferably greater than 98 wt %, more preferably greater than 99 wt %, and more preferably greater than 99.5 wt %. It is particularly preferred that the electrolyte consist essentially of, preferably consists of, ionic species.

The ionic liquid, deep eutectic solvent, and solid ionic conductor may additionally contain (e.g. be mixed with) one or more ionic species, typically a salt such as LiCl. These additional ionic species can be used, for example, to assist in the exfoliation of the graphitic negative electrode by intercalation into the graphite.

In embodiments the amount of (i), (ii) or (iii) and (iv) is greater than 55 wt % based on the total weight of the electrolyte. Suitably the electrolyte comprises (i), (ii) or (iii) and (iv) in an amount of greater than 55 wt %, preferably greater than 60 wt %, preferably greater than 65 wt %, preferably greater than 70 wt %, preferably greater than 75 wt %, preferably greater than 80 wt %, preferably greater than 85 wt %, preferably greater than 90 wt %, more preferably greater than 95 wt %, more preferably greater than 97 wt %, more preferably greater than 98 wt %, more preferably greater than 99 wt %, and more preferably greater than 99.5 wt %. It is particularly preferred that the electrolyte consists essentially of, preferably consists of (i), (ii) or (iii) and (iv).

Thus, it is preferred that (i), (ii) or (iii), optionally with (iv) are the only components of the electrolyte. It follows that suitably the electrolyte does not contain conventional non-ionic solvents such as for example DMSO (dimethyl sulfoxide), NMP (N-methyl pyrrolidone), DMF(N,N'-dimethyl formamide) and the like, and water. Even if the electrolyte contains non-ionic components those components are suitably present in an amount of less than 50 wt % based on the total weight of the electrolyte, preferably less than 45 wt %, preferably less than 40 wt %, preferably less than 35 wt %, preferably less than 30 wt %, preferably less than 25 wt %, preferably less than 20 wt %, preferably less than 15 wt %, preferably less than 10 wt %, preferably less than 5 wt %, preferably less than 3 wt %, more preferably less than 2 wt %, more preferably less than 1 wt % and most preferably less than 0.5 wt %. It is especially preferred that the electrolyte is essentially free of, preferably is free of (does not contain) non-ionic components.

Any suitable ionic liquid known in the art may be used. The choice of the ionic liquid will depend on the properties of the material and the desired reaction conditions. For instance, molten salts may be used provided the reaction is conducted at suitably high temperature. The term "molten salts" herein refers to salts that typically have a very high melting point, such as at least two hundred degrees above room temperature. Molten salts may include for example alkali-metal halides, alkali-metal carbonates, metal hydroxides, or metal oxides, preferably selected from $CaCl_2$, Cryolite, $Na_2CO_3$, $K_2CO_3$, LiCl, NaCl and KCl.

On the other hand, if lower temperature reaction conditions are desired, an ionic liquid having a low melting point will be required, such as a room temperature ionic liquid. Suitable ionic liquids having a low melting point can be provided by combining a cation selected from the group consisting of 1-alkyl-3-methylimidazolium, 1-alkylpyridinium, N-methyl-N-alkylpyrrolidinium and various ammonium ions (such as choline salts) and phosphonium cations with an anion selected from the group consisting of halides (e.g. F, Cl, Br and I), tetrafluoroborate, hexafluorophosphate, bistriflimide, triflate, tosylate formate, alkylsulfate, alkylphosphate and glycolate.

In the above embodiments the ionic liquid may for example be selected from the group consisting of 1-butyl-3-methylimidazolium tetrafluoroborate (i.e. [bmim][$BF_4$]), 1-butyl-3-methylimidazolium hexafluorophosphate (i.e. [bmim][$PF_6$]) and 1-butyl-3-methylimidazolium bis(trifluoromethylsulfonyl)imide (i.e. [bmim][$NTf_2$]). For example, the ionic liquid may be [bmim][$BF_4$] or [bmim][$PF_6$], such as [bmim][$PF_6$].

Particularly suitable is that the ionic electrolyte comprises or is a deep eutectic solvent (DES), which can be formed between different components capable of forming a eutectic mixture [Zhang 2012]. Typically the eutectic mixture is formed between one or more salts, as well as between salts/salt hydrates and hydrogen bond-donors.

Deep eutectic solvents have an advantage over conventional ionic liquids in that they are typically cheaper to make and generally less toxic. Deep eutectic solvents exhibit melting points much lower than the melting points of their constituent components and thus represent useful electrolyte materials, particularly where ambient temperatures and pressures are desired. For example, the melting point of the eutectic mixture is typically at least 10° C., suitably at least 20° C., suitably at least 30° C., suitably at least 50° C., suitably at least 75° C., and more suitably at least 100° C. lower than one or preferably all of their constituent components. However, molten eutectic mixtures, such as KOH—NaOH or CaO—$CaCl_2$ may also be used as the electrolyte if the reaction temperature is suitably high. Eutectic mixtures are preferred where molten salts are used as they form a molten liquid at a lower temperature than if the constituent molten salts were used as the electrolyte alone.

Suitably the eutectic solvent is selected from one or more of the following types:

Type I Eutectic—metal salt+organic salt (e.g. $ZnCl_2$+choline chloride)

Type II Eutectic—metal salt hydrate+organic salt (e.g. $CoCl_2$*$6H_2O$+choline chloride)

Type III Eutectic—organic salt+hydrogen bond donor (e.g. choline chloride+urea)

Type IV Eutectic—metal salt (hydrate)+hydrogen bond donor (e.g. $ZnCl_2$+urea)

Type III Eutectic is preferred.

An increasingly wide range of salts and hydrogen bond donors can be used for DES preparation as discussed by Zhang et al [Zhang 2012]:

| Halide Salts |
|---|
| 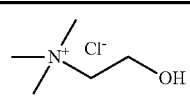
(ChCl) |
| 
(EtNH₃Cl)
ZnCl₂ |
| 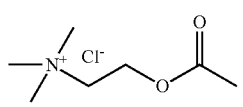
(AcChCl) |
| 
(TMACl) |
| 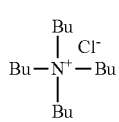
(TBACl) |
| 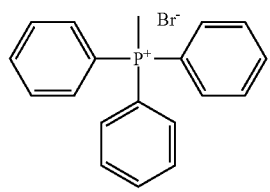 [SMILES: C[P+](c1ccccc1)(c1ccccc1)c1ccccc1 ; [Br-]]
(MeP(Ph)₃Br) |
| 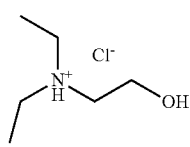
(Et₂(EtOH)ACl) |
| 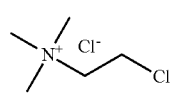
(ClChCl) |
| 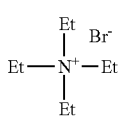
(TBABr) |
-continued
| |
|---|
| 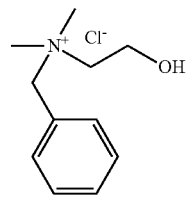 |
| Hydrogen bond donors |
| 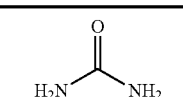 |
| 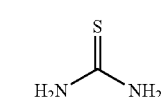 |
| 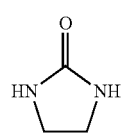 |
| 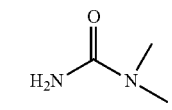 |
| 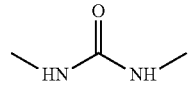 |
| 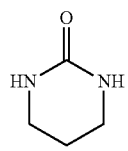 |
| 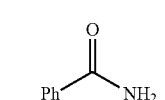 |
| 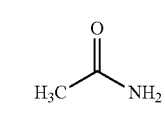 |
| 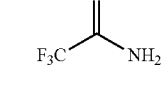 |
| 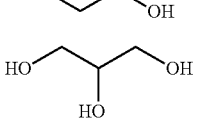 |
| 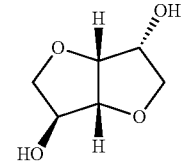 |

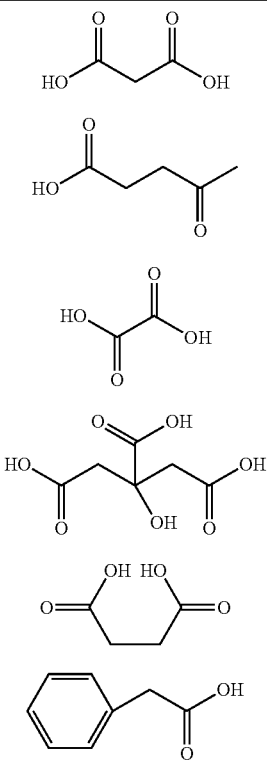

Zhang et al [Zhang 2012] confirmed that four types of DES can be identified using the general formula $R_1R_2R_3R_4N^+X^-.Y^-$ where Y is as follows for each of types I to III:

Type I: $Y=MCl_x$; where M=Zn, Sn, Fe, Al, Ga
Type II: $Y=MCl_x.yH_2O$; where M=Cr, Co, Cu, Ni, Fe
Type III: $Y=R_5Z$; wherein $Z$=—$CONH_2$, —COOH, —OH And a Type IV in which metal chlorides (e.g. $ZnCl_2$) are mixed with hydrogen bond donors such as urea, ethylene glycol, acetamide and hexanediol.

In the above embodiments the eutectic solvent may for example be selected from the group consisting of a mixture of $ZnCl_2$+choline chloride, a mixture of $CoCl_2*6H_2O$+choline chloride, a mixture of choline chloride+urea (typically in a ratio of 1:2), a mixture of $ZnCl_2$+urea, a mixture of choline chloride+malonic acid, a mixture of choline chloride+phenol, and a mixture of choline chloride+glycerol. For example, the eutectic solvent may be a mixture of choline chloride+urea, for instance in a mole ratio of 1:2.

Suitable electrolyte components include ammonium salt (such as an ammonium halide, e.g. choline chloride), alkali metal bicarbonate (e.g. such as $LiHCO_3$, $NaHCO_3$ or $KHCO_3$), alkali metal carbonate (such as $Li_2CO_3$, $Na_2CO_3$ or $K_2CO_3$) and an alkali metal halide (e.g. such as Li, Na or K halide, such as LiF or LiCl). In some embodiments, the electrolyte contains an ammonium salt (such as a halide, e.g. choline chloride), $LiHCO_3$, $NaHCO_3$, $Na_2CO_3$, $K_2CO_3$, or a sodium or potassium halides, or combinations thereof.

Typical ammonium salts for use in the electrolyte include tetraalkyl ammonium salts, (including tetrabutyl ammonium (TBA, $[(C_4H_9)_4N^+)$, tetraethyl ammonium (TEA, $(C_2H_5)_4N^+)$ and tetramethyl ammonium (TMA, $(CH_3)_4N^+)$ salts), trialkylammonium salts (such as tributyl ammonium $([(C_4H_9)_3NH^+)$, triethyl ammonium $((C_2H_5)_3NH^+)$, trimethyl ammonium $((CH_3)_3NH^+)$ salts) and dialkylammonium salts (such as dibutyl ammonium $([(C_4H_9)_2NH_2^+)$, diethyl ammonium $((C_2H_5)_2NH_2^+)$ and dimethyl ammonium $((CH_3)_2NH_2^+)$ salts). In such ammonium salts, the alkyl chains may contain up to 100 carbon atoms, more preferably up to 20 carbon atoms and most preferably up to 5 carbon atoms long. The alkyl chains may contain only a single carbon atom, but preferably contain at least two carbon atoms. The alkyl chains may all be the same, or may be different. Furthermore, a mixture of different ammonium ions may be used including a mixture of dialkylammonium cations, trialkylammonium cations and tetraalkyl ammonium cations. In such ammonium salts, the counter-ions may be relatively lipophilic ions, e.g. tetrafluoroborate ($BF_4^-$), perchlorate ($ClO^-$) or hexafluorophosphate ($PF_6^-$). Other soluble, inorganic ions may be used, such as tetraphenyl borate.

Accordingly, the electrolyte may be selected from the group consisting of 1-butyl-3-methylimidazolium tetrafluoroborate (i.e. [bmim][$BF_4$]), 1-butyl-3-methylimidazolium hexafluorophosphate (i.e. [bmim][$PF_6$]), 1-butyl-3-methylimidazolium bis(trifluoromethylsulfonyl)imide (i.e. [bmim][$NTf_2$]), a mixture of $ZnCl_2$+choline chloride, mixtures of $CoCl_2*6H_2O$+choline chloride, a mixture of choline chloride+urea (typically in a ratio of 1:2), a mixture of $ZnCl_2$+urea, a mixture of choline chloride+malonic acid, a mixture of choline chloride+phenol, a mixture of choline chloride+glycerol and solutions of ammonium salts (such as halides, e.g. choline chloride), alkali metal bicarbonates (e.g. $LiHCO_3$, $NaHCO_3$ and/or $KHCO_3$), alkali metal carbonates (e.g. $Li_2CO_3$, $Na_2CO_3$ and/or $K_2CO_3$) and alkali metal halides (e.g. Li, Na and/or K halides, such as LiF and/or LiCl).

In further embodiments, the electrolyte is selected from the group consisting of 1-butyl-3-methylimidazolium tetrafluoroborate (i.e. [bmim][$BF_4$]), 1-butyl-3-methylimidazolium hexafluorophosphate (i.e. [bmim][$PF_6$]), 1-butyl-3-methylimidazolium bis(trifluoromethylsulfonyl)imide (i.e. [bmim][$NTf_2$]), a mixture of $ZnCl_2$+choline chloride, a mixture of $CoCl_2*6H_2O$+choline chloride, a mixture of choline chloride+urea (typically in a ratio of 1:2), a mixture of $ZnCl_2$+urea, choline chloride+malonic acid, a mixture of choline chloride+phenol, a mixture of choline chloride+glycerol, and a solution including an ionic salt selected from an ammonium salt (such as an ammonium halide, e.g. choline chloride), $LiHCO_3$, $NaHCO_3$, $Na_2CO_3$, $K_2CO_3$, and a sodium or potassium halide.

In still further embodiments, the electrolyte is selected from the group consisting of 1-butyl-3-methylimidazolium tetrafluoroborate (i.e. [bmim][$BF_4$]), 1-butyl-3-methylimidazolium hexafluorophosphate (i.e. [bmim][$PF_6$]), 1-butyl-3-methylimidazolium bis(trifluoromethylsulfonyl)imide (i.e. [bmim][$NTf_2$]), a mixture of $ZnCl_2$+choline chloride, a mixture of $CoCl_2*6H_2O$+choline chloride, a mixture of choline chloride+urea (typically in a ratio of 1:2), a mixture of $ZnCl_2$+urea, a mixture of choline chloride+malonic acid, a mixture of choline chloride+phenol, and a mixture of choline chloride+glycerol.

In typical embodiments, the electrolyte is selected from the group consisting of 1-butyl-3-methylimidazolium tetrafluoroborate (i.e. [bmim][$BF_4$]), 1-butyl-3-methylimidazolium hexafluorophosphate (i.e. [bmim][$PF_6$]), 1-butyl-3-methylimidazolium bis(trifluoromethylsulfonyl)imide (i.e. [bmim][$NTf_2$]), and a mixture of choline chloride+urea (typically in a ratio of 1:2), for example 1-butyl-3-methylimidazolium hexafluorophosphate (i.e. [bmim][$PF_6$]) or a mixture of choline chloride+urea (typically in a ratio of 1:2).

It is particularly preferred that the electrolyte comprises a mixture of choline chloride and urea, suitably in a mole ratio of about 1:2. It is especially preferred that the electrolyte comprises a mixture of choline chloride and urea and one or more ionic species. It is further preferred that the electrolyte consists essentially of, preferably consists of, a mixture of choline chloride and urea and one or more ionic species. Suitably the ionic species is a Li salt, suitably LiCl. Thus, a very preferred electrolyte consists essentially of, preferably consists of, a mixture of choline chloride and urea and LiCl.

The electrolyte may be, or may include, a solid ionic conductor (solid electrolyte), such as a dry polymer electrolyte or a solid ceramic electrolyte.

Suitably the electrolyte includes organic ions, which organic ions suitably intercalate into the graphite negative electrode. Thus, preferably the organic ions are cations. The organic ions can come from (be a component part of) the ionic liquid, deep eutectic solvent or solid ionic conductor, or from ionic species mixed with the ionic liquid, deep eutectic solvent or solid ionic conductor (i.e. the electrolyte comprises (iv) one or more ionic species).

Suitably the electrolyte includes metal ions, which metal ions suitably intercalate into the graphite negative electrode. Thus, preferably the metal ions are cations. The metal ions can come from (be a component part of) the ionic liquid, deep eutectic solvent or solid ionic conductor, or from ionic species mixed with the ionic liquid, deep eutectic solvent or solid ionic conductor.

In embodiments the electrolyte contains both organic ions and metal ions, suitably organic cations and metal cations.

The organic ions are preferably alkylammonium cations, particularly tetralkyl, trialkyl and dialkyl ammonium cations.

Tetraalkyl ammonium cations are preferable, including tetrabutyl ammonium (TBA, $[(C_4H_9)_4N^+]$), tetraethyl ammonium (TEA, $(C_2H_5)_4N^+$) and tetramethyl ammonium (TMA, $(CH_3)_4N^+$). The alkyl chains may contain up to 100 carbon atoms, more preferably up to 20 carbon atoms and most preferably up to 5 carbon atoms long. The alkyl chains may contain only a single carbon atom, but preferably contain at least two carbon atoms. The alkyl chains may all be the same, or may be different. Furthermore, a mixture of different cations maybe used.

Dialkylammonium cations and trialkylammonium cations may be also used in the invention, including tributyl ammonium ($[(C_4H_9)_3NH^+]$), triethyl ammonium ($(C_2H_5)_3NH^+$), triemethyl ammonium ($(CH_3)_3NH^+$), dibutyl ammonium ($[(C_4H_9)_2NH_2^+]$), diethyl ammonium ($(C_2H_5)_2NH_2^+$) and diemethyl ammonium ($(CH_3)_2NH_2^+$), The alkyl chains may contain up to 100 carbon atoms, more preferably up to 20 carbon atoms and most preferably up to 5 carbon atoms long. The alkyl chains may contain only a single carbon atom, but preferably contain at least two carbon atoms. The alkyl chains may all be the same, or may be different.

Furthermore, a mixture of different cations may be used, including a mixture of dialkylammonium cations, trialkylammonium cations and tetraalkyl ammonium cations.

Other organic cations suitable for use in the present invention may include alkylphosphonium cations, such as tetraalkyl phosphonium cations.

The counter-ions for the alkylammonium cations may be, e.g. tetrafluoroborate ($BF_4^-$), perchlorate ($ClO_4^-$) or hexafluorophosphate ($PF_6^-$). Other soluble, inorganic ions may be used, such as tetraphenyl borate or chloride.

The metal ions can be selected from, for example, iron, tin and lithium ions, and thus can be $Fe^{2+}$, $Fe^{3+}$, $Sn^{2+}$ and $Li^+$. The metal ions may also be selected from $K^+$, $Na^+$ and $Al^{3+}$ and rare earth ions.

The counter-ions for the metal ions may be chloride or any other soluble anions (such as the counter-ions listed above for the alkylammonium cations, e.g. tetrafluoroborate ($BF_4^-$), perchlorate ($ClO_4^-$) or hexafluorophosphate ($PF_6^-$)). The counter-ions should not be those that can attack the graphite.

It may be preferred that the electrolyte is formed by making a eutectic mixture of the organic ion salt (e.g. alkylammonium salt) and metal ion salt. This allows the method of the invention may be carried out at a range of cell operating temperatures.

In some embodiments, the concentration of the alkyl ammonium cations may be a minimum of 1 mM, 0.1 M, 0.2 M or 0.5 M. The maximum concentration may be 2M, 1.5M or 1M.

In some embodiments, the concentration of the metal cations may be a minimum of 1 mM, 0.1 M, 0.2 M or 0.5 M. The maximum concentration may be 2M, 1.5M or 1M.

Cell Potential and Current Density

The working potential of the cell will be at least that of the standard potential for reductive intercalation. An overpotential may be used in order to increase the reaction rate and to drive cations into the galleries of the graphite at the negative electrode. Preferably an overpotential of 1 mV to 15 V is used against a suitable reference as known by those skilled in the art, more preferably 1 mV to 12 V, more preferably 1 mV to 10 V and more preferably 1 mV to 5 V. In cells with only two terminals, and no reference, a larger potential may be applied across the electrodes but a significant amount of the potential drop will occur over the cell resistance, rather than act as an overpotential at the electrodes. In these cases the potential applied may be up to 20V or 30V.

An advantage of using the electrolyte described herein is that a wider potential window can be accessed as compared to electrolyte compositions where the major component is a conventional organic solvent of the sort disclosed in e.g. WO2012/120264. In particular, this can be useful where functionalization of the graphene or graphite nanoplatelet structures is desired, for example hydrogenation, for example to produce graphane. Thus, in embodiments the potential applied to the negative electrode (i.e. the electrode at which the cathodic process of intercalation occurs) is in the range −30V to 30V, suitably from −20 to 30V, suitably from −20 to 20V, suitably from −15 to 20 V, suitably from −15 to 15V, suitably from −12 to 15V, suitably −12 to 12V and preferably from about −10 to about 10V.

Naturally, even when the potential applied to the negative electrode is negative, the potential difference (ΔV) across the positive and negative electrodes will still be such that cathodic processes occur at the negative graphitic electrode. This means that in practice if the negative electrode is at a negative potential, the positive electrode will be at a less negative potential or at zero or a positive potential.

Typically, current is allowed to pass between the electrodes at a potential difference of from 1 to 10 V, such as from 2 to 8 V, for example 2 to 5 V, e.g. 3 to 5 V. For instance, the current allowed to pass between the electrodes may be at a potential difference of about 1 V, about 2 V, about 3 V, about 4 V, about 5 V, about 6 V, about 7 V, about 8 V, about 9 V or about 10 V. Typically, the current is allowed to pass between the electrodes at a potential difference of about 3 V.

Cycling of Potential

The voltage applied across the electrodes may be cycled or swept. That is, the potential can be varied so as to increase or decrease it. For example, the potential is changed in a first direction (it increases or decreases) for a first period and then is changed in a second direction opposite to the first direction for a second period. Thus, if the potential is increased for a first period, it can be decreased for a second period. The first and second periods can be the same or different. Preferably they are the same. The magnitude of the change (increase or decrease) can be the same or different. Preferably it is the same. The rate of change in each period can be the same or different. Preferably it is the same. Suitably the steps of changing in a first period and changing in a second period are repeated, preferably at least 2 times, more preferably at least 5 times, more preferably at least 10 times, more preferably at least 30 times. For each repeated cycle the direction, magnitude and rate of change and the duration of the first and second periods can be selected independently. Preferably they are the same.

Thus, embodiments include a cyclical variation of the potential.

Suitably the variation (e.g. cyclical variation) of the potential is such that cathodic processes continue to occur at the negative electrode. That is, suitably the polarity of the electrodes is not switched. This cathodic (cyclical) variation of the potential can, for example, be used to provide intercalation of two different cations, e.g. an organic cation and a metal cation.

In practice, the minimum value of the potential during any such (cyclical variation) is the open-circuit potential.

In embodiments the variation of potential includes swapping/switching the polarity of the electrodes such that the negative electrode becomes the positive electrode and vice versa. This means that the cathodic process on the negative electrode will stop during the part of the method in which the polarity is reversed.

Suitably the switching of polarity is cyclical such that it is repeated, preferably at least 2 times, more preferably at least 5 times, more preferably at least 10 times, more preferably at least 30 times.

Suitably the switching interval is in the range 10 seconds to 1 hour, suitably 10 seconds to 30 minutes, suitably 10 seconds to 20 minutes, suitably 10 seconds to 15 minutes, suitably 10 seconds to 10 minutes, suitably 30 seconds to 10 minutes, suitably 30 seconds to 5 minutes, preferably 30 seconds to 3 minutes.

Suitably the switching interval remains constant (e.g. switching occurs every X minutes for the period during which potential switching occurs).

Suitably the period after a potential switch (i.e. between a first switch and a second switch) is at least 10 minutes, suitably at least 20 minutes, suitable at least 30 minutes, suitably at least 40 minutes, suitably at least 50 minutes, suitably at least 60 minutes, suitably at least 90 minutes, suitably at least 120 minutes.

The present inventors have observed that the use of voltage switching in the context of the specific type of electrolyte described herein can lead to improved formation and/or isolation of graphene and related materials. This is believed to be because intercalated ions are urged out of the galleries of the graphite as a result of the reversal of the potential and this in turn can cause flexing of the graphitic layers and hence encourage separation of the layers.

In embodiments, alternating current can be used to allow for both fast intercalations and de-intercalations.

In particularly preferred embodiments both the electrodes are graphitic and the potential is varied so that electrodes change from positive to negative and vice versa. In this embodiment the cationic exfoliation would occurs at both electrodes, depending on the polarity of the electrode during the voltage cycle.

The current density at the negative electrode will be controlled through a combination of the electrode's surface area and overpotential used. The method can also be carried out under current control.

Operating Temperature

The cell is operated at a temperature which allows for production of the desired material.

The cell may be operated at a temperature of at least 10° C., preferably at least 20° C. The maximum cell operating temperature may be 100° C., and more preferably 90° C., 80° C., 70° C. or 50° C. In some embodiments, the cell may be operated at a temperature of at least 30, 40 or 50° C. The maximum cell operating temperature may be as high as 120° C. The optimum operating temperature will vary with the nature of the electrolyte. Operating the cell up to the boiling point of the electrolyte may be carried out in the present invention.

The temperature within the electrochemical cell may thus be at least 10° C., preferably at least 20° C. For instance, the temperature within the electrochemical cell may be cell room temperature. In some embodiments, the temperature within the electrochemical cell is at least 30° C., 40° C., 50° C., 60° C., 70° C., 80° C., 90° C. or 100° C. In the case of molten salts, the temperature within the cell may for example be up to 1500° C. In some embodiments, the temperature within the cell does not exceed 1000° C., 900° C., 800° C. or 700° C., preferably the cell operating temperature does not exceed 650° C., 600° C., 550° C., 500° C., 450° C., 400° C., 350° C., 300° C., 250° C., 200° C., 150° C. or more preferably 120° C. In other embodiments, the temperature within the cell does not exceed 110° C., more preferably the temperature within the cell does not exceed 100° C., 90° C., 80° C., 70° C., 60° C. or more preferably 50° C.

Operating Pressure

The electrochemical cell may be operated at any suitable pressure that allows for production of the desired graphene/graphite nanoplatelet structures/graphane.

Operating Atmosphere

The electrochemical cell may be operated under any suitable gaseous atmosphere. For example, the electrochemical cell in processes of the invention may be operated under an anhydrous atmosphere, such as under nitrogen, and/or argon. In alternative embodiments, the electrochemical cell is operated under air.

Duration of Reaction

The electrochemical process may be operated for a length of time adequate to provide a desirable yield of graphene and/or graphite nanoplatelet structures and/or graphane. The duration of the process typically refers to the length of time that a current is passed between the electrodes prior to isolation of the graphene/graphite nanoplatelet structures/graphane. The current may be passed between the electrodes continuously or intermittently, typically continuously.

In some embodiments, the length of time that a current is passed between the electrodes is greater than one minute, preferably greater than 5 min, 10 min, 20 min, 30 min, 40 min, 50 min preferably greater than one hour. Typically, the reaction duration from 1 h to 72 h, such as from 1 h to 48 h, for instance 1 h to 24 h. In further embodiments, the length of time that a current is passed between the electrodes is from 1 h to 10 h, 1 h to 5 h or 1 h to 4 h. Typically the length of time that a current is passed between the electrodes is about 3 h. In alternative embodiments, the reaction is continuous.

Recovery of Cations

In one embodiment, the cations used for the exfoliation are recovered after exfoliation. The cations may be recovered by washing and for heating of the exfoliated material, electrochemical reduction of the cations, ultrasonic energy treatment of the exfoliated material, displacement from the exfoliated material by surfactants or combinations thereof.

Further Method Steps

In one embodiment, organic ions may be added in a second stage, in order to favour the exfoliation of graphite through a process of polymerization and expansion between the graphene layers. Suitable organic ions include monomers for polymerisation possessing electron-withdrawing groups such as nitrile, carboxyl, phenyl, and vinyl.

The graphene, graphite nanoplatelet structures having a thickness of less than 100 nm, and graphane produced by the method of the invention may be separated from the electrolyte by a number of separation techniques, including:

(a) filtering;

(b) using centrifugal forces to precipitate the graphene or graphite nanoplatelet structures or graphane;

(c) collecting the graphene or graphite nanoplatelet structures or graphane at the interface of two immiscible solvents; and (d) sedimentation.

The electrochemically exfoliated graphene or graphite nanoplatelet structures or graphane may be further treated after exfoliation. For example, the materials may be further exfoliated using ultrasonic energy and other techniques known to those skilled in the art to decrease the flake size and number of graphene/graphane layers.

In some embodiments, the electrochemical intercalation may be repeated in order to achieve full exfoliation.

The graphite at the negative electrode may be functionalised electrochemically prior to its exfoliation, for example, by oxidation in nitric acid or fluorination using hydrofluoric acid. In these cases the negative electrode would become the positive electrode during the functionalisation. In some circumstances, as noted above, the voltage may be reversed to cycle the electrochemical exfoliation and functionalisation steps.

In embodiments, the method includes the step of recovering the electrolyte, which suitably includes separating solid material (typically graphene and graphene related products) from the electrolyte. In embodiments, the method includes the step of re-using the electrolyte in a subsequent electrochemical cell process.

In some embodiments, the process further includes the step of isolating the graphene/graphite nanoplatelet structures/graphane. For instance, in some embodiments the present invention provides a process as described above wherein the process further includes the steps of isolating the graphene and/or graphite nanoplatelet structures and/or graphane produced.

Where the graphene/graphite nanoplatelet structures/graphane are suspended in the electrolyte or have fallen to the floor of the electrochemical cell, isolation of the graphene/graphite nanoplatelet structures/graphane can be achieved by separation from the electrolyte according to a number of separation techniques, including:

(a) filtering;

(b) using centrifugal forces to precipitate/accumulate the graphene or graphite nanoplatelet structures or graphane; and (c) collecting the graphene or graphite nanoplatelet structures or graphane at the interface of two immiscible solvents.

In some embodiments the graphene/graphite nanoplatelet structures/graphane are isolated by filtration. Typically, the graphene/graphite nanoplatelet structures/graphane are isolated by filtration using a fine membrane material, such as Anopore™ inorganic membrane (i.e. Anodisc™ which is commercially available from GE Healthcare).

The process may include the further step of manipulating the graphene/graphite nanoplatelet structures/graphane either prior to isolation (such as in the electrochemical cell), or after isolation from the electrochemical cell. For example, the graphene/graphite nanoplatelet structures/graphane may be washed to remove contaminants prior to or following isolation, for instance to remove residual electrolyte from the product surface. In embodiments, the process includes the step of forming and/or shaping the graphene/graphite nanoplatelet structures/graphane prior to, or following, isolation, such as forming and/or shaping the graphene/graphane into an article.

In embodiments, the process includes the step of incorporating the graphene and or graphite nanoplatelet structures or graphane into an article.

In a further aspect of the invention is provided graphene and/or graphene nanoplatelet structures and/or graphane prepared according to a process as described in any of the above aspects and embodiments. In a further aspect, the invention provides a composition including graphene and/or graphite nanoplatelet structures and/or graphane prepared according to a process as described in any of the above aspects and embodiments. In a still further aspect is provided an article including said composition or said graphene and/or graphite nanoplatelet structures and/or graphane prepared according to a process as described in any of the above aspects and embodiments, or, optionally, a derivative of said composition or graphene and/or graphite nanoplatelet structures and/or graphane.

The skilled person will understand that the above embodiments are described by way of example only. Other embodiments falling within the scope of the claims will be apparent to the skilled reader. It will be appreciated that the features specified in each aspect and embodiment may be combined with other specified features in other embodiments, to provide further embodiments.

The present invention is described in more detail by way of example only with reference to the following Examples.

EXAMPLES

General Electrochemical Procedure

All the electrochemical experiments were conducted in 50 ml air tight glass beakers. The beaker was sealed using rubber plug or custom-made plastic lid. The electrodes are fixed on the lid so that the electrode distance is fixed at 5 mm at the start of the run. To control the surface area of the electrodes, the electrodes were attached to stainless steel rods that are allowed to move vertically using a M4 screw threaded onto the lid.

Analysis of Graphene by Raman Spectroscopy

All the Raman spectroscopy was conducted using a 633 nm excitation laser.

It is well established in the literature that Raman spectroscopy can be used to determine the number of layers that a carbon flake possesses through the shape, intensity and position of the D (~1350 cm$^{-1}$), G (~1580 cm$^{-1}$) and 2D (~2700 cm$^{-1}$) peaks (the 2D peak may be alternatively referred to as the G' peak).

The exact positions of the Raman peaks depend on the excitation wavelength used and the level of doping in the sample [Ferrari 2006]. In general, the Raman spectrum for single layer graphene comprises a 2D peak which can be fitted with a single component and is similar or higher in intensity than the G peak. The 2D peak for monolayer graphene occurs at approximately 2637 cm$^{-1}$ when measured using a 633 nm excitation laser. As the number of layers increase, the 2D peak decreases in relative intensity to the G peak.

The 2D peak would be expected to be centred at approximately 2637, 2663, 2665, 2675 and 2688 cm-1 for 1-layer, 2-layer, 3-layer, many-layer and graphite respectively using a 633 nm laser to measure graphene flakes deposited on an oxide-covered silicon wafer.

The intensity of the D peak relative to the G peak also provides an indication of the number of structural defects such as graphene edges and sub-domain boundaries in the material produced. A D peak to G peak ratio (ID/IG) of around 0.2 may be expected for pristine graphene and the lower the ratio the better the quality material produced [Malard 2009].

Example 1

Figure 1:
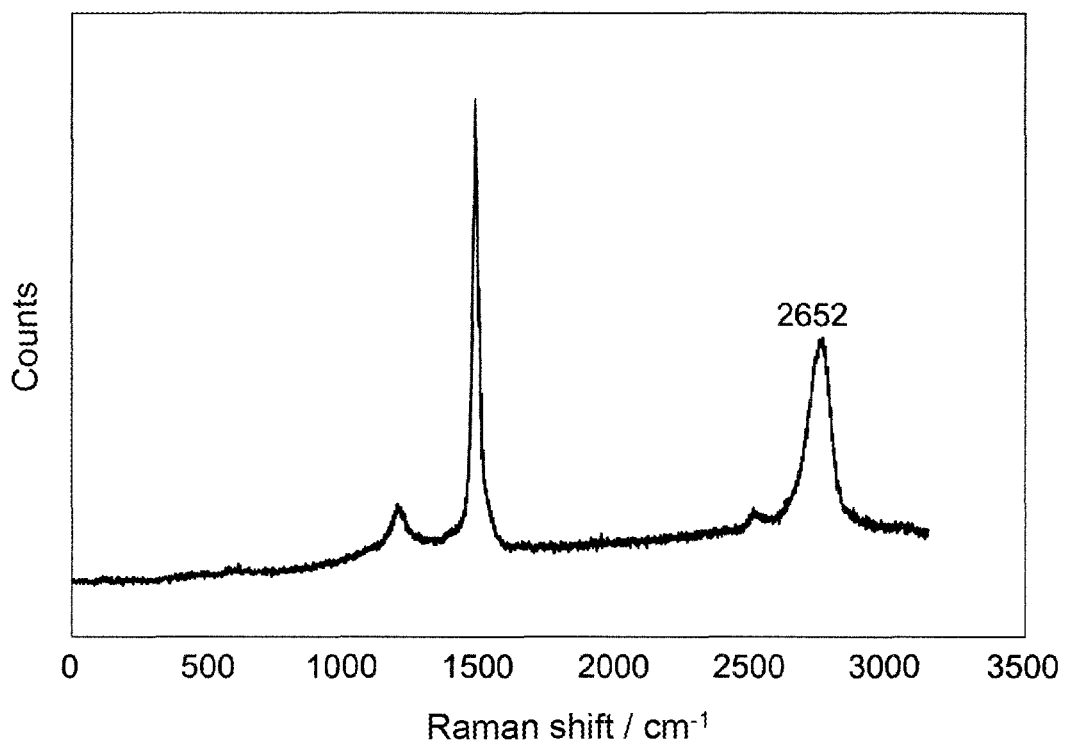
FIG. 1 shows a typical Raman spectrum of the powder produced in Example 1.

A cell was assembled having graphite rods as working electrode, Li as counter electrode, and Ag/AgCl as reference electrode. The liquid electrolyte was an eutectic mixture of 1:2 Choline chloride: Urea with 2 M LiCl in the electrolyte. A potential of 10 V was applied to the working electrode versus Ag/AgCl for 8 hours. The Raman spectrum (FIG. 1) of the exfoliated carbonaceous material collected from the electrolyte shows few layer graphene features, i.e. large G band at 1585 cm$^{-1}$ and large symmetrical 2D band at ~2650 cm$^{-1}$.

There was no evidence of breakdown/decomposition of the liquid electrolyte.

Example 2

Eutectic mixture of 1:2 Choline chloride: Urea were prepared in a glovebox under inert atmosphere. About 2 mole/liter of LiCl was added to the eutectic liquid to form the electrolyte. A cell was assembled having a graphite rod wrapped in a membrane as working electrode, Li as a counter electrode, and Ag/AgCl as reference electrode. A potential of 2.5 V was applied versus Ag/AgCl for 8 hours. The cell was continuously flushed with Ar gas.

The first step of the exfoliation/hydrogenation process is believed to be the reduction of Et$_3$N either electrochemically on the negative graphite electrode, or chemically by the adsorbed or deposited lithium:

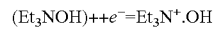
$(Et_3NOH)+ + e^- = Et_3N^+ \cdot OH$

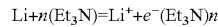
$Li + n(Et_3N) = Li^+ + e^-(Et_3N)n$

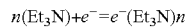
$n(Et_3N) + e^- = e^-(Et_3N)n$

The ability of Li and Et$_3$N to intercalate between the graphene layers in the graphite structure makes these reactions not limited only to the surface of the graphite electrode, but to some micron in the depth direction, depending on the density of the rod.

The second step is believed to be the formation of a carbanion complex with the evolving of trimethylamine:

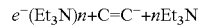
$e^-(Et_3N)n + C = C^- + nEt_3N$

The carbanion complex then decomposes by the reaction with the hydroxyl radical resulting in the formation of a covalent hydrogenated carbon derivative:

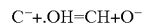
$C^- + \cdot OH = CH + O^-$

This reaction competes with the formation of hydrogen, and/or lithium hydride:

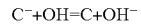
$C^- + OH = C + OH^-$

$Li^+ + OH^- = LiOH$

The last reaction seems to be more dominant at high potential. The macroscopic appearance of hydrogenated graphene was very similar to that of the pristine samples, only the increased stability of the aqueous suspension, i.e., the significantly lower rate of sedimentation, indicated the modification of the surface.

Figure 2:
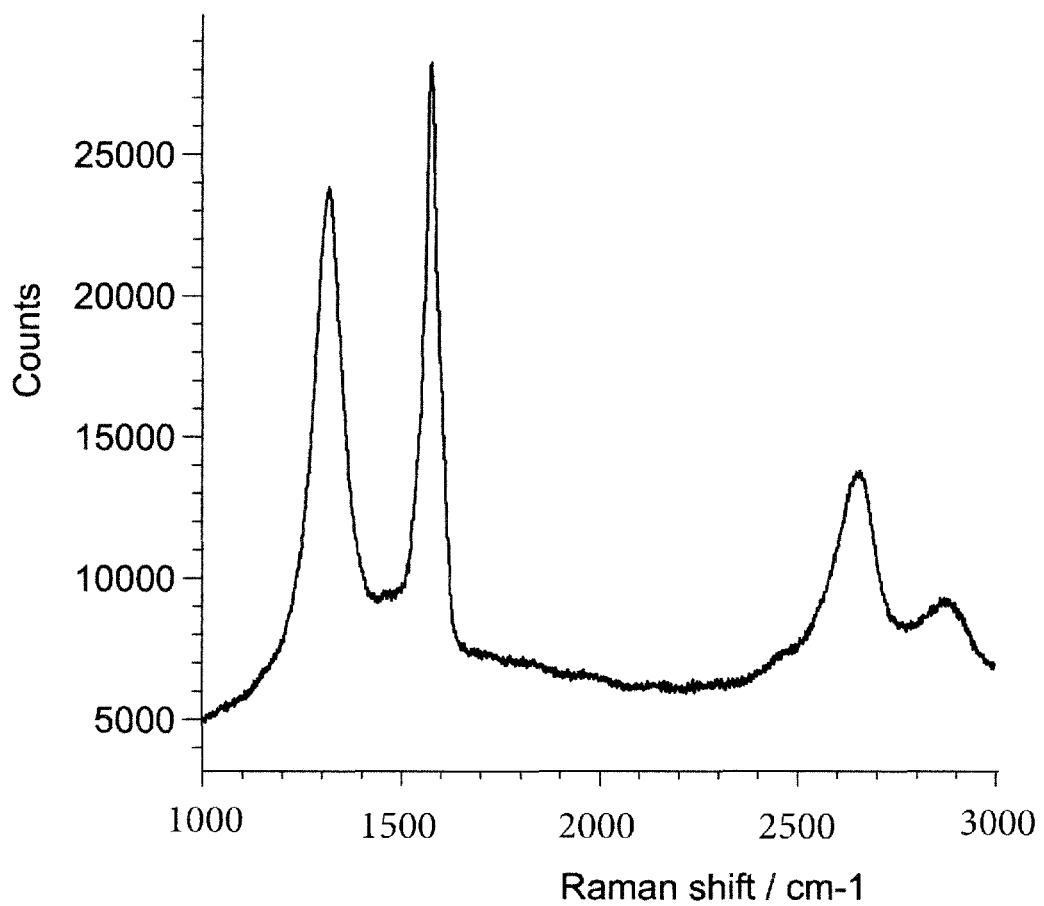
FIG. 2 shows a typical Raman spectrum of the powder produced in Example 2.
Figure 3:
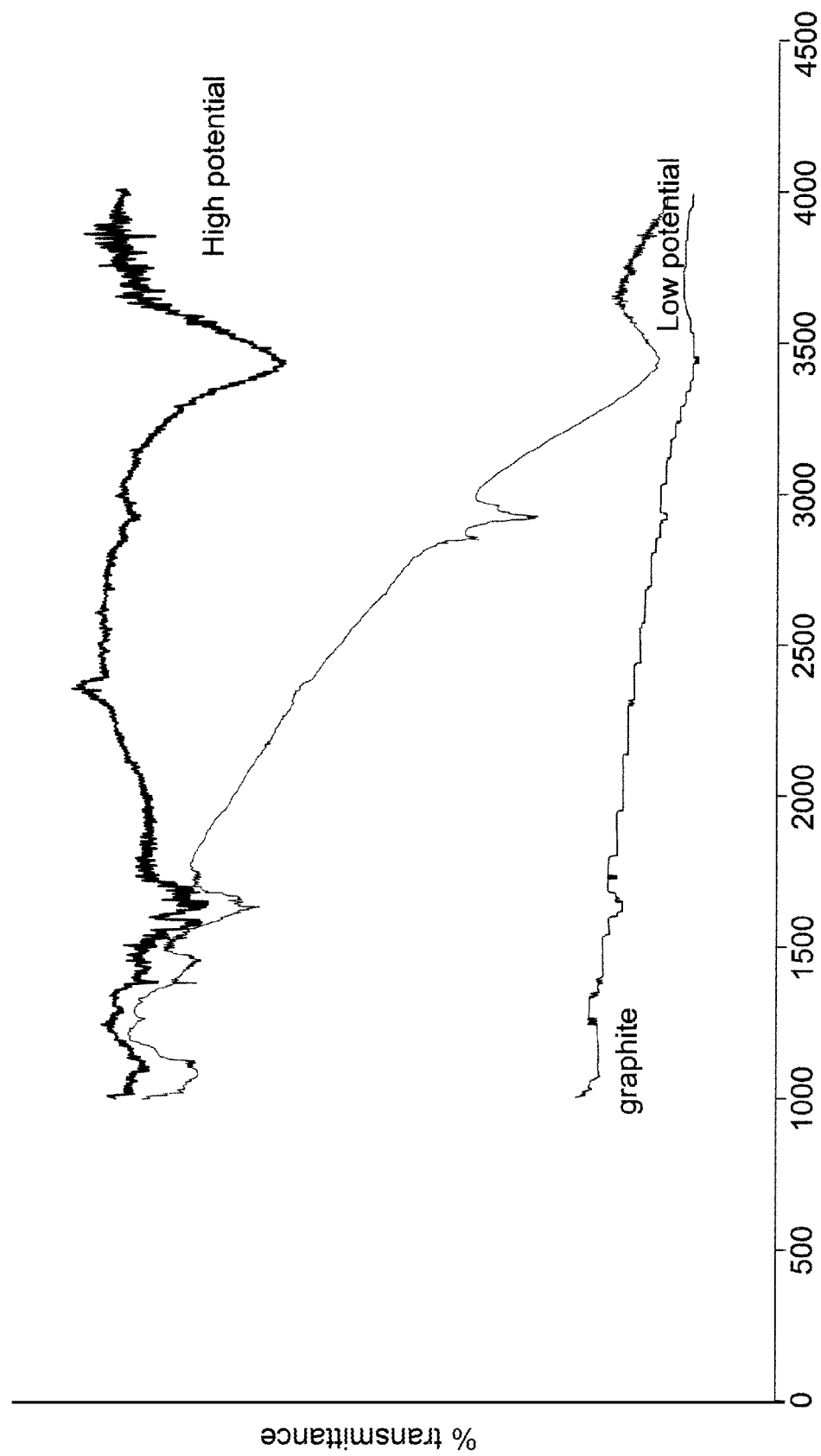
FIG. 3 shows a typical FTIR spectrum of the powder produced in Example 2.
Figure 4:
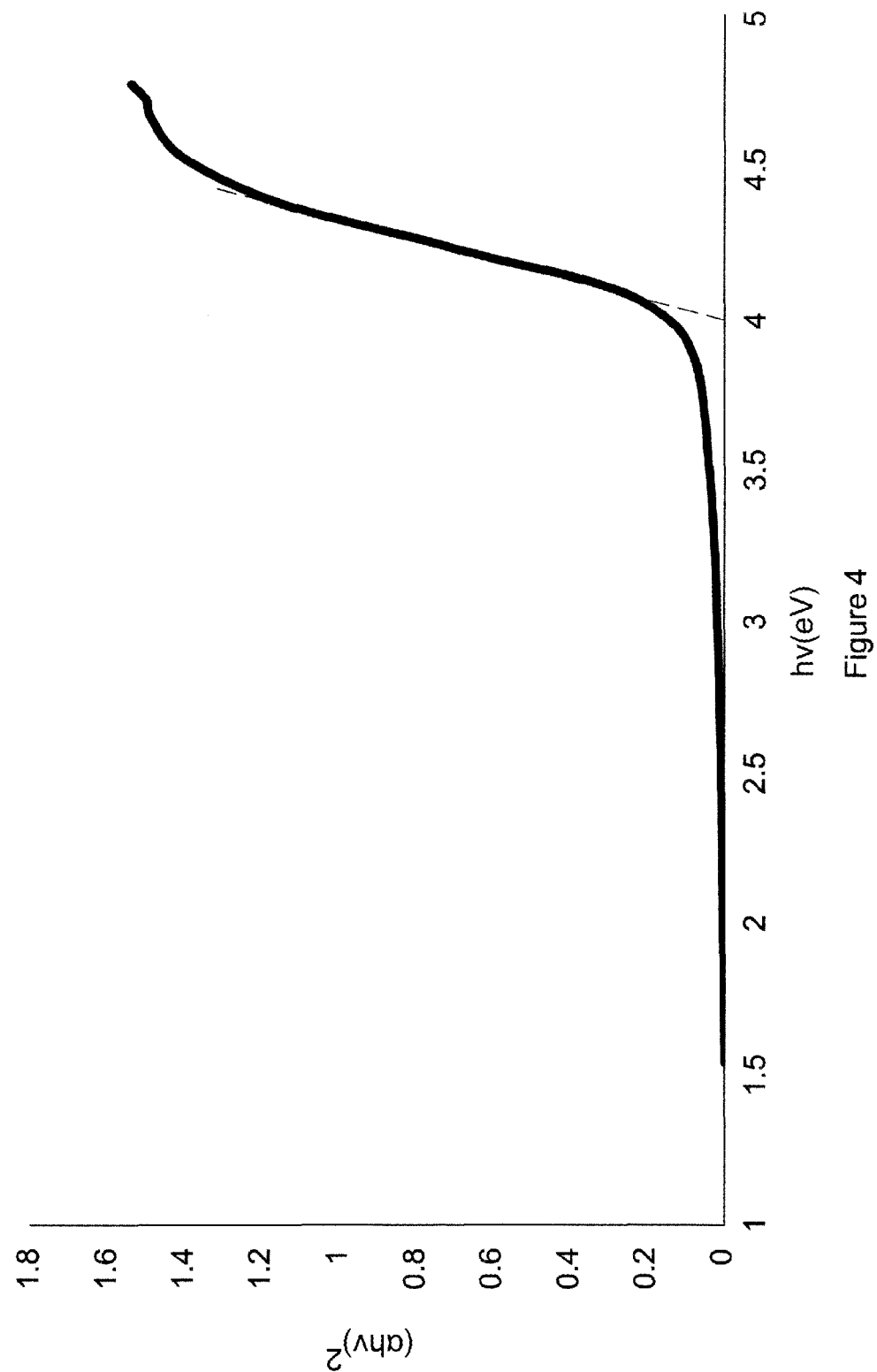
FIG. 4 shows a band gap analysis of the powder produced in Example 2.

The same experimental procedure was used as Example 1, but using an applied potential of −2.5 V. The Raman spectrum (FIG. 2) shows a Large D band at ~1330 cm$^{-1}$, a significant decrease in the 2D band, and merging of the D+D' band at ~2900 cm$^{-1}$, which indicates hydrogenation. FTIR analysis (FIG. 3) shows distinctive peaks at 2884 cm$^{-1}$ and 2912 cm$^{-1}$ corresponding to the aliphatic C—H stretch vibrations. These peaks were not observed in this region for graphite nor for the graphene prepared in Example 1. The band gap of the hydrogenated sample was determined (FIG. 4) to be ~4 eV by using UV-Vis spectroscopy and Tauc's equation.

These results, including the determination of the 4 eV band gap demonstrates that graphane had been formed. This is particularly significant because it means that hydrogenation of the graphite surface occurred in-situ. In other words there is no need for a second step of hydrogenation. This demonstrates not only a new efficient route for the preparation of graphane but also that the use of the specific type of electrolyte described herein together with a graphitic negative electrode provides wide flexibility for functionalization of the graphite-derived material. This versatility is a valuable step forward in the scale-up of the production of graphene and graphene-type materials.

There was no evidence of breakdown/decomposition of the liquid electrolyte.

Example 3

A eutectic mixture of ferrous chloride and triethylamine hydrochloride ($Et_3NHCl$) was prepared under inert atmosphere at room temperature. Two graphite rods were used as electrodes. A potential difference of 15 V was applied for 1 hour with the current being limited to 0.5 A. The electrode polarity was switched every 3 minutes. By the end of the electrolysis, the brown colour of the electrolyte was changed into black. After the end of the run, the electrolyte was leached in a multistep process using acidified water, distilled water, ethanol, and acetone. The resulted powder was filtered out using 100 nm pore diameter filter paper.

Figure 5:
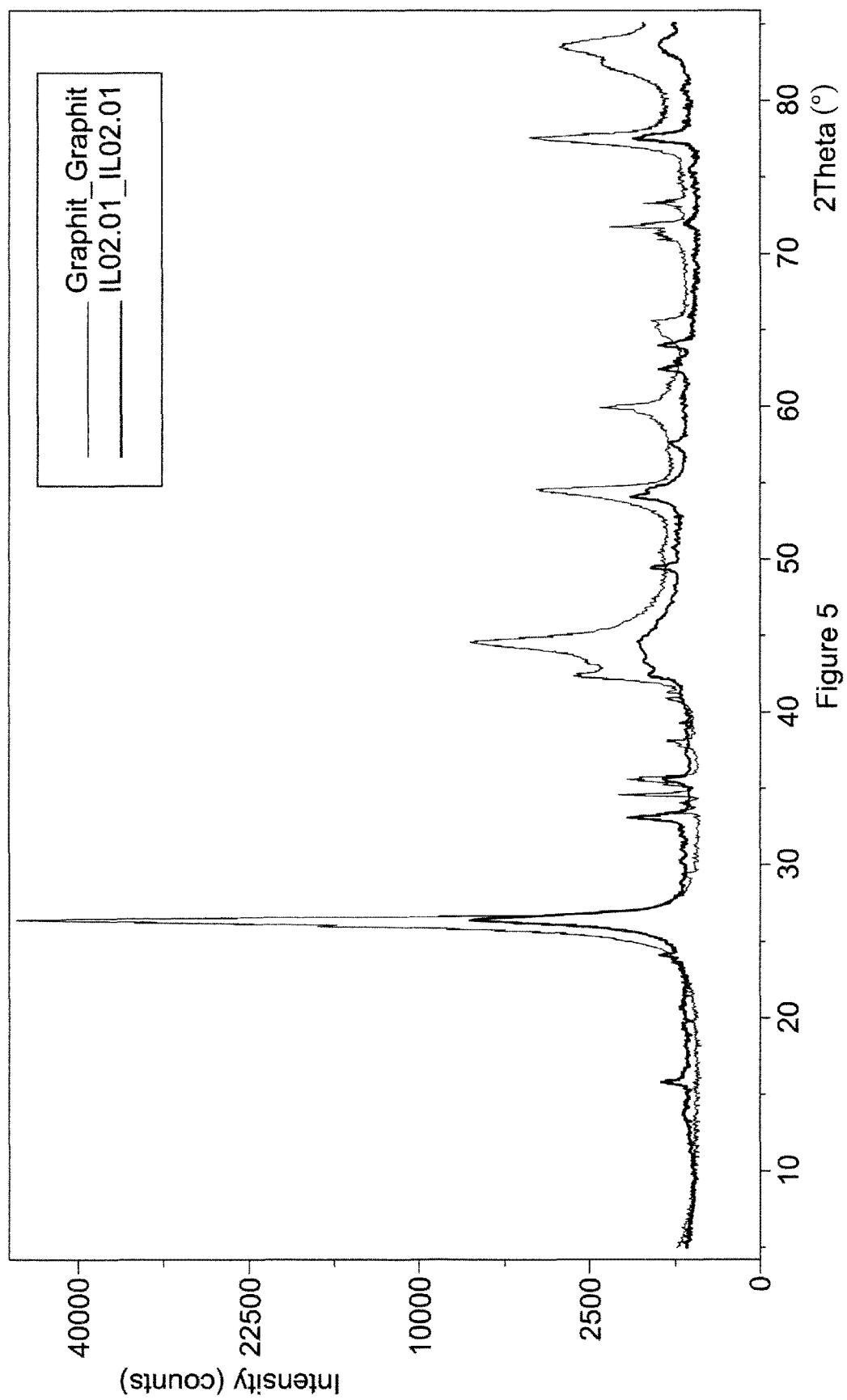
FIG. 5 shows an XRD Pattern of the powder produced in Example 3 (lower trace) compared with the original graphite (upper trace)
Figure 6:
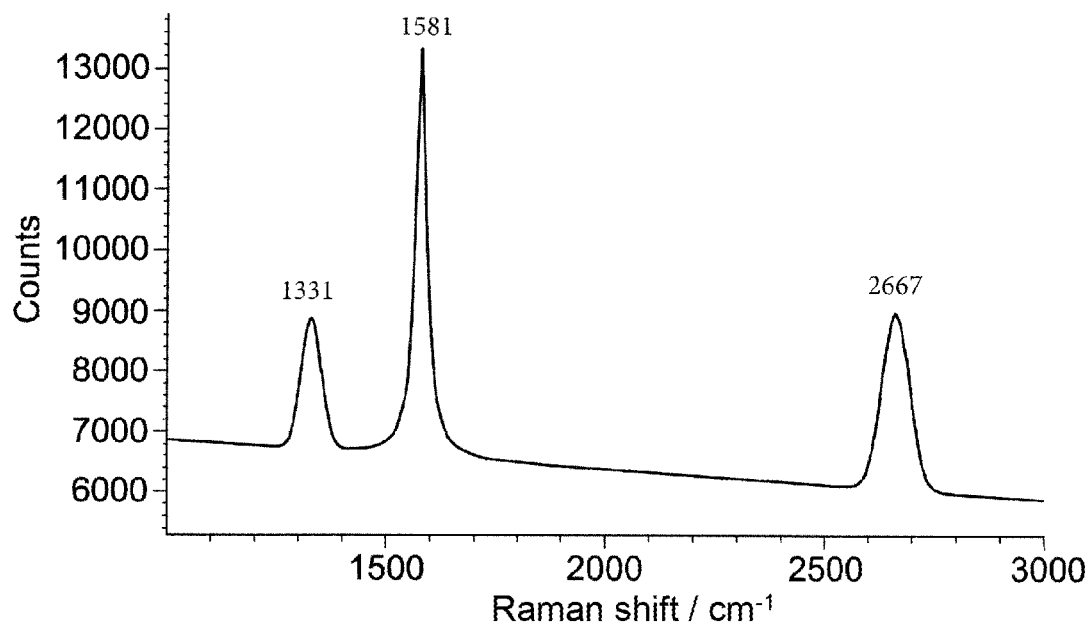
FIG. 6 shows a typical Raman spectrum for the powder produced in Example 3.
Figure 7:
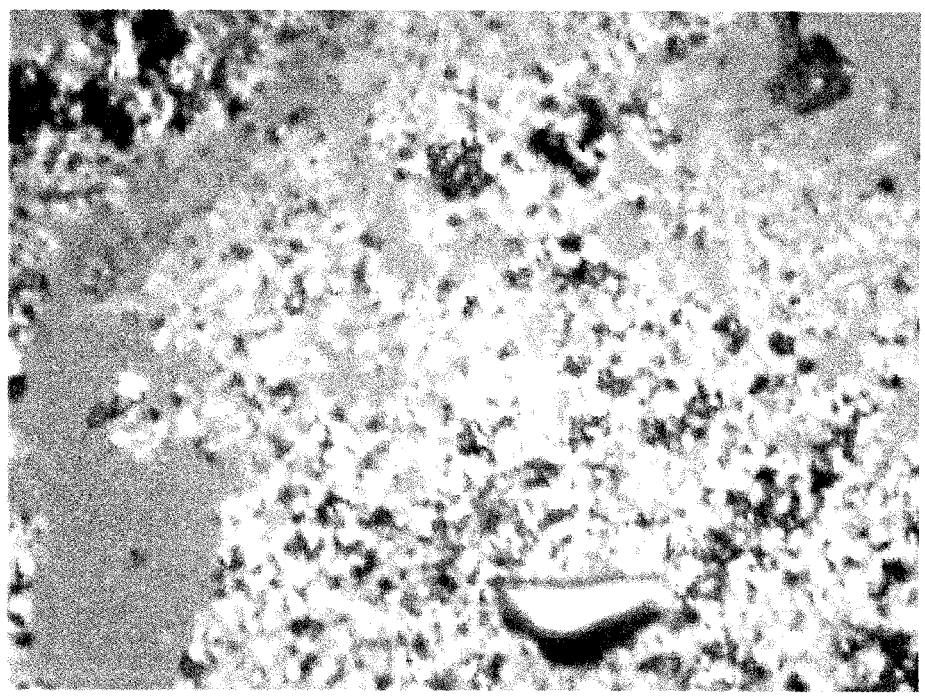
FIG. 7 shows an SEM image of powder produced in Example 3.

The produced powder was characterised using XRD and Raman spectroscopy. The XRD pattern of the obtained powder is illustrated in FIG. 5 together with that of the initial graphite powder used as the electrode (upper trace is graphite starting material; lower trace is the collected powder). The strong 002 peak that characterises the π-π stacked layers in the graphite was weakened (e.g. less intense) after electrolysis indicating some disruption in the π-π stacked layers. The 2D band in the Raman spectrum (FIG. 6) is at 2667 $cm^{-1}$ and the full width at half-maximum (FWHM) of the 2D band is 64.4 $cm^{-1}$ which is very close to the characteristic values of four layer graphene. An SEM image of the powder is shown in FIG. 7.

There was no evidence of breakdown/decomposition of the liquid electrolyte.

Example 4

The experimental procedure in Example 1 was followed except that the polarity of the potential difference was reversed every 30 seconds over a 15 minute period. Thus, for half of the process (including the first and last phases) the graphitic electrode was the negative electrode and the electrode on which graphene was produced.

Figure 8:
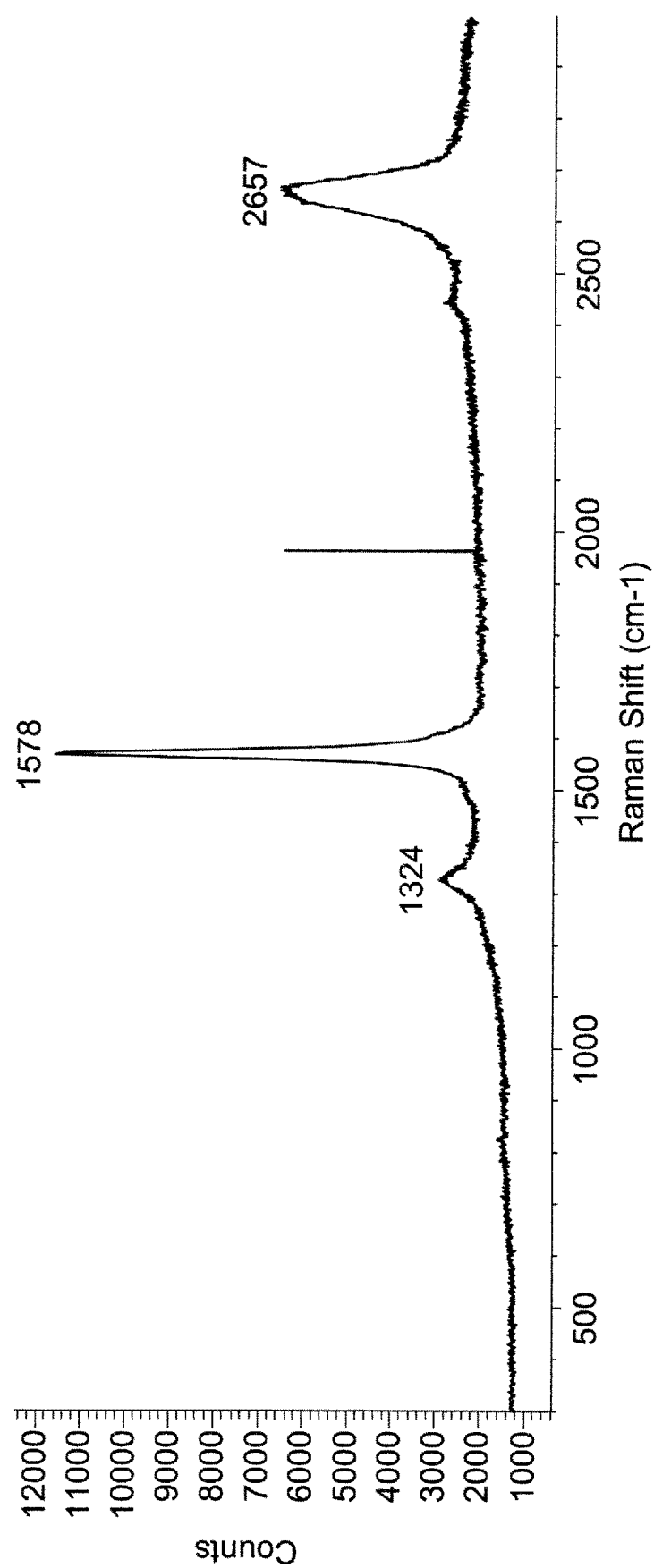
FIG. 8 shows a typical Raman spectrum for the powder collected on the cathode in Example 4.

The Raman spectrum is shown in FIG. 8. Clearly the position of the 2D peaks was shifted to 2657 $cm^{-1}$. Although this value is close to the typical position of 2D band in bilayer graphene, the width of this peak is much higher (72.5 $cm^{-1}$).

There was no evidence of breakdown/decomposition of the liquid electrolyte.

Example 5

Figure 9:
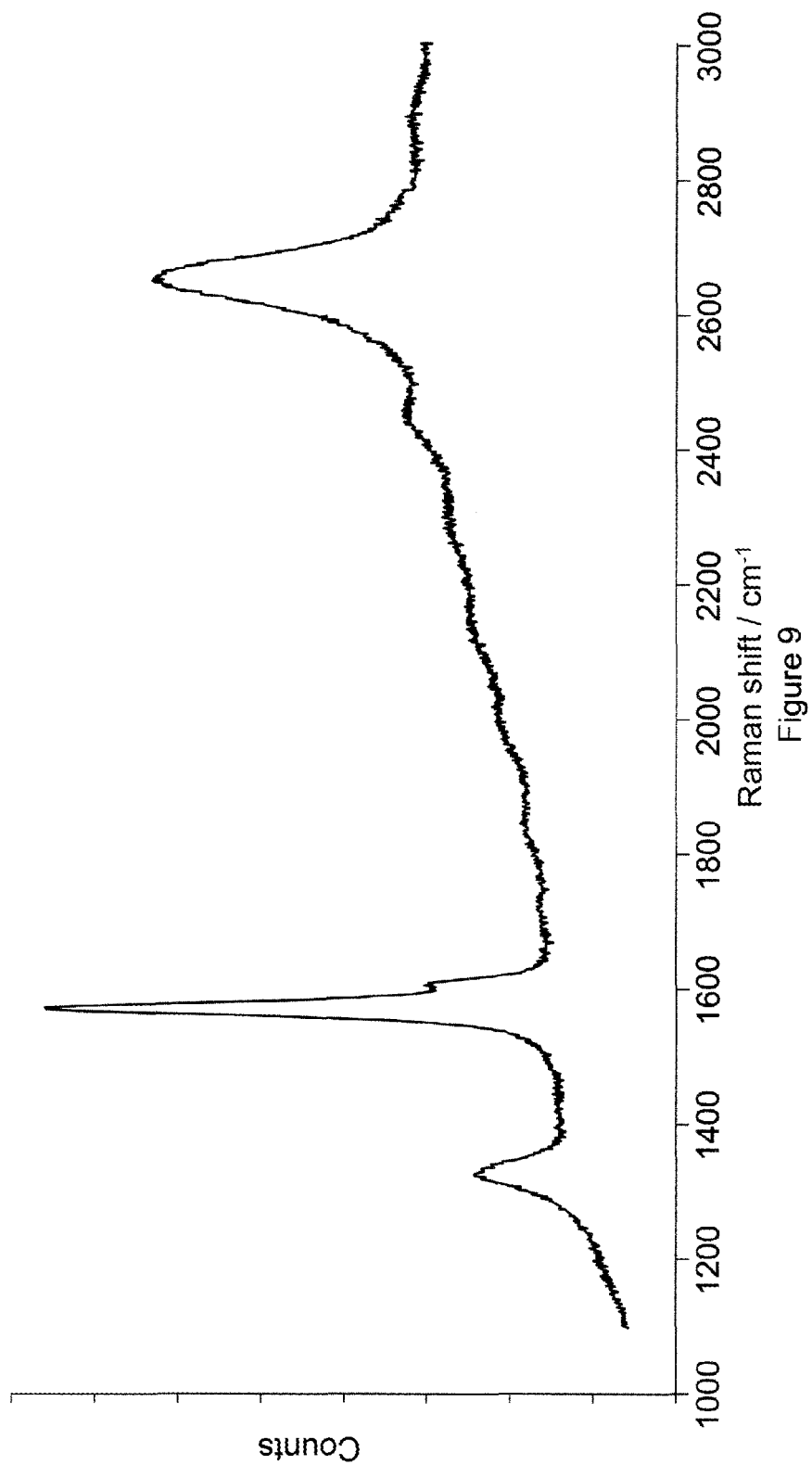
FIG. 9 shows a typical Raman spectrum for the powder collected on the cathode in Example 5.

The experimental procedure in Example 4 was followed except that but the electrolyte used was a mixture of aluminium chloride-triethylamine hydrochloride. The Raman spectrum shows (FIG. 9) graphenic structure with intense 2D band centred at 2654 $cm^{-1}$.

There was no evidence of breakdown/decomposition of the liquid electrolyte.

Example 6

A cell composed of a graphite working electrode, Pt counter electrode and Ag/AgCl reference electrode was used. The electrolyte was an eutectic mixture of $SnCl_2$—$Et_3NHCl$. The potential was switched between −5 to 5 V versus the reference every 2 minutes for 2 hours. The Raman analysis shows intense symmetric 2D band at 2652 $cm^{-1}$.

There was no evidence of breakdown/decomposition of the liquid electrolyte.

Example 7

Figure 10:
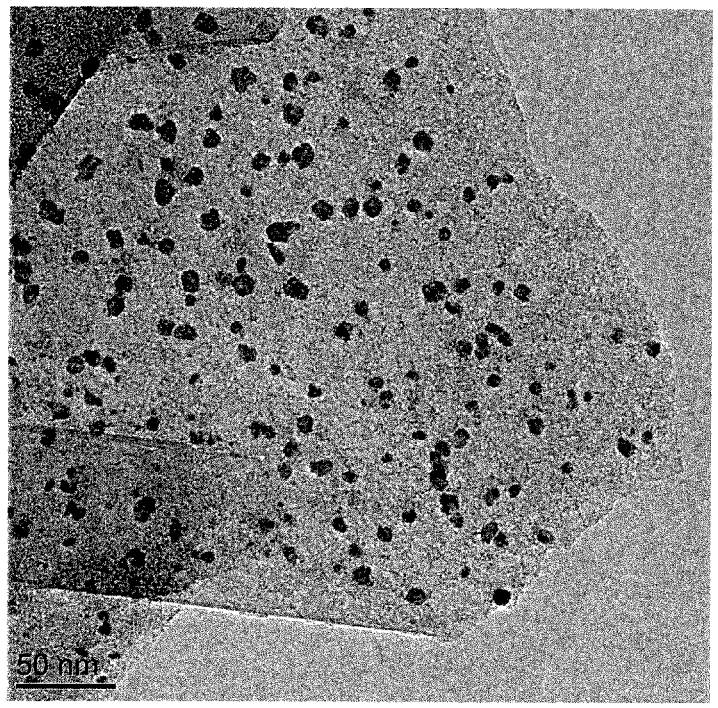
FIG. 10 shows a TEM image of iron nanoparticles on the graphene surface from the powder collected in Example 7.

Natural graphite powder was pressed into a pellet, wrapped by a silver wire into a nickel rod current collector. The pellet was then wrapped in a porous membrane, and the whole assemblage served as working electrode. The counter and the reference electrodes were Pt and Ag/AgCl respectively. The electrolyte was eutectic mixture of ferrous chloride and triethylamine hydrochloride as in Examples 3 and 5. The applied potential was switched between 2.8 and −2.8 V with the interval of 1 minute for the first hour. The potential at the working electrode was then held at −2.8 V for the next 30 minutes. The cathode assemblage was removed from the cell, washed with distilled water and dilute acetic acid to remove any residual salt. To minimize the electrochemical corrosion during washing, the pellets were cathodically protected by applying 1.2 V versus Ag/AgCl electrode. The samples were then rinsed in ethanol and dried in a vacuum oven. The TEM image (FIG. 10) showed nanoparticles of iron on the graphene surface. The magnetic properties of the resultant hybrid were easily detected by a magnet.

Thus, the method of the present invention provides a convenient, safe and efficient way of producing, in a single step, hybrid materials comprising graphene and metal-containing nanoparticles. As is clear from the TEM image, dispersion of the nanoparticles is good.

There was no evidence of breakdown/decomposition of the liquid electrolyte.

Example 8

Figure 11:
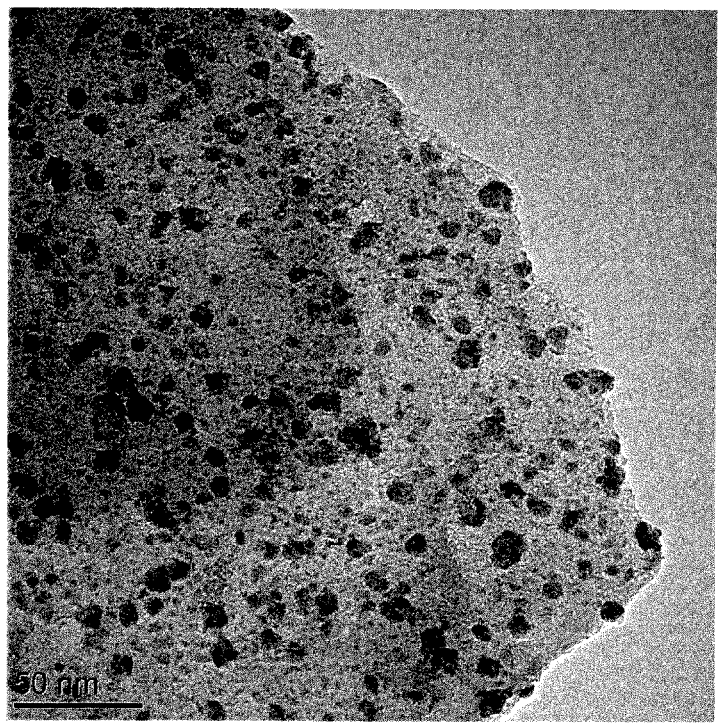
FIG. 11 shows a TEM image of Sn nanoparticles on the graphene surface from the powder collected in Example 8.

The experimental procedure in Example 7 was followed except that a eutectic mixture of $SnCl_2$-$Et_3NHCl$ was used as electrolyte. The TEM image (FIG. 11) revealed the deposition of Sn species nanoparticles on the surface of the graphene.

Again, this demonstrates the versatility of the method of the present invention. The provision of well dispersed nanoparticles, particularly metal-containing nanoparticles and especially Sn-containing nanoparticles in the context of a "clean" and scalable process represents a valuable contribution to the art.

There was no evidence of breakdown/decomposition of the liquid electrolyte.

Example 9

Figure 12A:
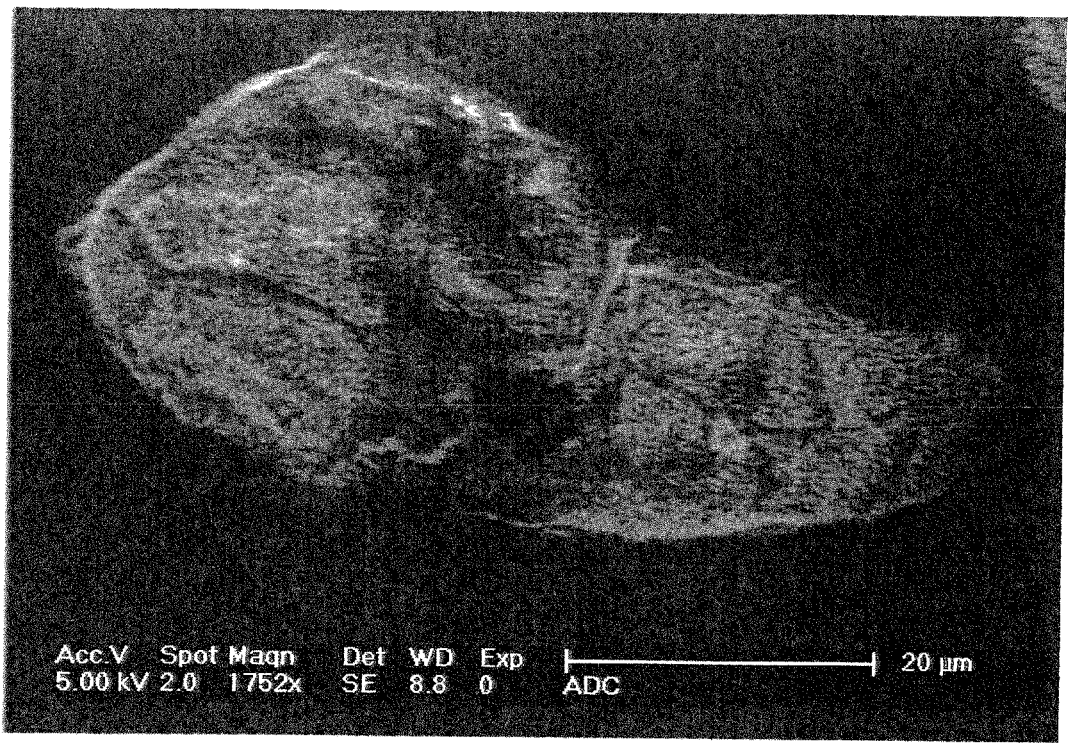
FIG. 12A shows a TEM image of Sn-containing species from the powder collected in Example 9.
Figure 12B:
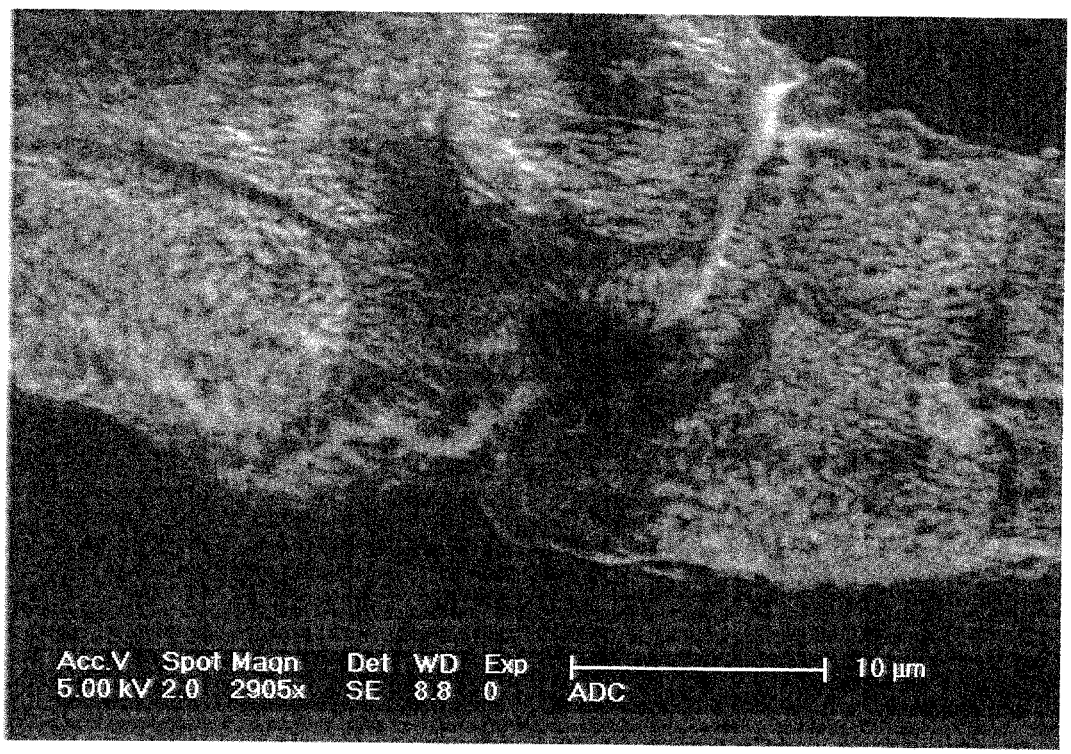
FIG. 12B shows an enlarged TEM image of Sn-containing species from powder collected in Example 9.

The experimental procedure in Example 6 was followed except that a potential deference of 4 V was applied between graphite cathode and Pt anode for 2 hours. The SEM images (FIGS. 12A and 12B) showed graphene sheets heavily decorated by Sn-containing species.

There was no evidence of breakdown/decomposition of the liquid electrolyte.

Example 10

A two-terminal cell was used. The cathode was made of graphite rod wrapped in a membrane and the anode was Pt wire. The electrolyte used was 1 M LiCl in a mixture of methyl urea and choline chloride (2:1 by weight). The applied voltage was 15 V for 4 hours. The powder was subjected to several steps of washing and drying before conducting Raman analysis. The Raman collected spectrums indicate a symmetric 2D band at ~2655 cm$^{-1}$ confirming the graphenic nature of the produced powder.

Example 11

The procedure of Example 10 was followed except that the electrolyte was 1M LiCl in acetamine-choline chloride eutectic mixture. The Raman spectrum of the produced powder showed typical features of graphene materials with G, and 2D bands at ~1885 and ~2660 cm$^{-1}$ respectively.

Example 12

The electrochemical experiments were conducted in a molten salt reactor consisting of a vertical tubular alumina vessel with 70 mm inside diameter and 500 mm height placed inside a vertical tube furnace. About 200 mm of the top part of the vessel was kept outside the furnace and the vessel was sealed by silicone stopper that worked as the lid. The electrolyte used was a mixture of aluminum sodium chloride ($NaAlCl_4$) and triethylamine hydrochloride (9:1 by wight) at 180° C. The electrochemical experiment was conducted using a two-terminal programmable power supply, the anode was a Pt wire, and the cathode was a graphite rod. Both electrodes were attached to 3 mm diameter stainless steel rods that work as a current collectors and was attached to the reactor lid. The electrolyte was heated at 1° C./min up to the target temperature and kept at that temperature for 30 minutes before introducing the cell electrodes. A potential difference of 3 V was applied for 4 hours. The cell was then was allowed to cool in the furnace under a continuous flow of argon gas. The cell was then removed from the furnace, and washed with water and dilute hydrochloric acid solution to dissolve the solidified salts. The liquor was then filtered to separate the produced powder. The powder was then dried over night at 60° C. and subjected to analysis. The G band (~1,580 cm$^{-1}$) and 2D band are clearly visible in all cases. It was possible to detect flakes with intense symmetric 2D band at 2650 cm$^{-1}$.

Example 13

The procedure of Example 12 was followed except that the electrolyte was a eutectic mixture of LiCl—KCl at 600° C. The applied voltage was switched between 0.5 V and 3V every 20 second for 4 hours. The powdered collected from the electrolyte was found to be few layers graphene from analysis of the Raman spectrum.

Other Experiments

Data from preliminary experiments indicates that the general electrochemical approach described herein can also be used to exfoliate other 2D materials, especially those having graphite-like structures. An example of a suitable 2D material is $MoS_2$. Indeed, the present inventors have acquired TEM and AFM data which support a conclusion that exfoliation of $MoS_2$ occurs in the electrochemical cell.

REFERENCES

The following documents are all incorporated herein by reference.

[Novoselov 2004] Electric field effect in atomically thin carbon films, K. S. Novoselov et al., Science, 2004, 5296, pp 666-669.

[Ruoff 2009] Chemical methods for the production of graphenes, S. Park and R. S. Ruoff, Nature Nanotechnology, 2009, DOI:10.1038/nnano.2009.58

[Bae 2010] Roll-to-roll production of 30-inch graphene films for transparent electrodes, S. Bae et al. Nature Nanotechnology, 2010, DOI: 10.1038/NNANO.2010.132

[Ang 2009] High-Throughput Synthesis of Graphene by Intercalation-Exfoliation of Graphite Oxide and Study of Ionic Screening in Graphene Transistor, P. K. Ang et al., ACS Nano, 2009, 3(11), pp. 3587-3594

[Wang 2010] Direct exfoliation of natural graphite into micrometre size few layers graphene sheets using ionic liquids, X. Wang et al., Chem. Commun., 2010, 46, pp. 4487-4489

[Liu 2008] N. Liu et al, One-Step Ionic-Liquid-Assisted Electrochemical Synthesis of Ionic-Liquid-Functionalized Graphene Sheets Directly from Graphite. Adv. Funct. Mater. 2008, 18, pp. 1518-1525

[Lu 2009] One-Pot Synthesis of Fluorescent Carbon Nanoribbons, Nanoparticles, and Graphene by the Exfoliation of Graphite in Ionic Liquids, ACS Nano, 2009, 3(8) pp. 2367-2375

[Simonet 1977] J. Simonet and N. Lund, Electrochemical Behavious of Graphite Cathodes in the Presence of Tetralkylammonium Cations, J. Electroanal. Chem., 1977, 75, pp. 719-730

[Hsu, 1995] W. K. Hsu, J. P. Hare, M. Terrones, H. W. Kroto and D. R. M. Walton, Condensed phase nanotubes, Nature, 377, 687 (1995)

[Kinloch, 2003] I. A. Kinloch et al, E lectrolytic, TEM and Raman studies on the production of carbon nanotubes in molten NaCl, Carbon, 2003, 41, pp. 1127-1141

[Coleman 2008 & 2009] Y. Hernandez, et al, Nat. Nanotechnol., 2008, 3, 563; M. Lotya, et al, J. Am. Chem. Soc., 2009, 131, 3611.

[Valles 2008] Valles, C. et al. Solutions of negatively charged graphene sheets and ribbons. J. Am. Chem. Soc. 130, 15802-15804 (2008).

[Ferrari 2006] Ferrari, A. C. et al. Raman Spectrum of Graphene and Graphene Layers. Phys Rev Lett, 97 (2006), 187401

[Hao 2010] Hao, Y et al., Probing Layer Number and Stacking Order of Few-Layer Graphene by Raman Spectroscopy, Small, 2010, 6(2), 195-200

[Wang 2011] Wang, J., et al., High-yield synthesis of few-layer graphene flakes through electrochemical expansion of graphite in propylene carbonate electrolyte, JACS, 2011, 133, 8888-8891

[Gao 2008] Gao, L., et al., Electrodeposition of Aluminum from AlCl3/Et3NHCl Ionic Liquids, Acta Physico-Chimica Sinica, Volume 24, Issue 6, June 2008, Pages 939-944

[Simate 2010] The production of carbon nanotubes from carbon dioxide: challenges and opportunities, Simate, G. S. et al. Journal of Gas Chemistry, 2010, 19(5), 453;

[DeWulf 1989] Electrochemical and Surface Studies of Carbon Dioxide Reduction to Methane and Ethylene at Copper Electrodes in Aqueous Solution, J. Electrochem. Soc. 1989, 136(6), 1686.

[Suzuki 2012] Journal of Physics: Conference Series, 2012, 379(1):012038.

[Malard 2009] Malard L. M. et al., Raman spectroscopy in graphene, Phys. Rep. 473, 51-87 (2009).

[Zhong 2012] Y. L. Zhong, T. M. Swager, J. Am. Chem. Soc. 2012, 134, 17896-17899

[Huang 2012] Huang et al, J. Mater. Chem., 2012, 22, 10452-10456

[Zhang 2012] Zhang et al, Chem. Soc. Rev., 2012, 41, 7108-7146.

[Geim 2009] Geim A K. Graphene: Status and Prospects. Science 2009; 324:1530.

[Matis 2011] Matis B R, Burgess J S, Bulat F A, Friedman A L, Houston B H, Baldwin J W. Surface Doping and Band Gap Tunability in Hydrogenated Graphene. ACS Nano 2011; 6:17.

[Jaiswal 2011] Jaiswal M, Yi Xuan Lim C H, Bao Q, Toh C T, Loh K P, √ñzyilmaz B. Controlled Hydrogenation of Graphene Sheets and Nanoribbons. ACS Nano 2011; 5:888.

[Gao 2011] Gao H, Wang L, Zhao J, Ding F, Lu J. Band Gap Tuning of Hydrogenated Graphene: H Coverage and Configuration Dependence. The Journal of Physical Chemistry C 2011; 115:3236.

[Sofo 2007] Sofo J O, Chaudhari A S, Barber G D, Graphane: A two-dimensional hydrocarbon. Phys. Rev. B 2007; 75.

[Elias 2009] Elias D C, Nair R R, Mohiuddin T M G, Morozov S V, Blake P, Halsall M P, Ferrari A C, Boukhvalov D W, Katsnelson M I, Geim A K, Novoselov K S. Control of Graphene's Properties by Reversible Hydrogenation: Evidence for Graphane. Science 2009; 323:610.

[Ryu 2008] Ryu S, Han M Y, Maultzsch J, Heinz T F, Kim P, Steigerwald M L, Brus L E. Reversible Basal Plane Hydrogenation of Graphene. Nano Letters 2008; 8:4597.

[Guisinger 2009] Guisinger N P, Rutter G M, Crain J N, First P N, Stroscio J A. Exposure of Epitaxial Graphene on SiC(0001) to Atomic Hydrogen. Nano Letters 2009; 9:1462.

[Wang 2010] Wang Y, Xu X, Lu J, Lin M, Bao Q, Ozyilmaz B, Loh K P. Toward High Throughput Interconvertible Graphane-to-Graphene Growth and Patterning. ACS Nano 2010; 4:6146.

[Poh 2012] Poh H L, Sanek F, Sofer Z, Pumera M. High-pressure hydrogenation of graphene: towards graphane. Nanoscale 2012; 4:7006.

[Yang 2012] Yang Z, Sun Y, Alemany L B, Narayanan T N, Billups W E. Birch Reduction of Graphite. Edge and Interior Functionalization by Hydrogen. Journal of the American Chemical Society 2012; 134:18689.

[Schäfer] Schäfer R A, Englert J M, Wehrfritz P, Bauer W, Hauke F, Seyller T, Hirsch A. On the Way to Graphane— Pronounced Fluorescence of Polyhydrogenated Graphene. Angewandte Chemie International Edition 2013; 52:754.

The invention claimed is:

1. A method for production in an electrochemical cell of one or more of graphene, graphite nanoplatelet structures having a thickness of less than 100 nm, and graphane, wherein the electrochemical cell comprises:
   (a) a negative electrode which is graphitic;
   (b) a positive electrode which may be graphitic or another material; and
   (c) an electrolyte that is selected from:
      (i) an electrolyte comprising a deep eutectic solvent which comprises at least two constituent components, said deep eutectic solvent having a deep eutectic solvent melting point that is at least 10° C. lower than a component melting point of one of said constituent components, wherein the deep eutectic solvent is present in an amount that is greater than 90 wt % based on total weight of the electrolyte; and
      (ii) an electrolyte comprising a deep eutectic solvent which comprises at least two constituent components, said deep eutectic solvent having a deep eutectic solvent melting point that is at least 10° C. lower than a component melting point of one of said constituent components, the electrolyte further comprising one or more additional ionic species, wherein the deep eutectic solvent and the additional ionic species are present in an amount that is greater than 90 wt % based on total weight of the electrolyte;
   and wherein the electrolyte includes a mixture of different cations;
   and wherein the method comprises the step of passing a current through the electrochemical cell to intercalate ions into the graphitic negative electrode so as to exfoliate the graphitic negative electrode.

2. The method of claim 1, wherein the electrolyte is free of organic solvent and water.

3. The method of claim 1, wherein the electrolyte includes a metal cation and an organic cation.

4. The method of claim 1, wherein the amount of the deep eutectic solvent that is present in the electrolyte of (c)(i), or the amount of the deep eutectic solvent and the additional ionic species that is present in the electrolyte of (c)(ii), is greater than 99 wt % based on the total weight of electrolyte.

5. The method of claim 1, wherein the deep eutectic solvent comprises choline chloride and urea in a mole ratio of about 1:2.

6. The method of claim 1, wherein the electrolyte further comprises one or more salts selected from metal cation-containing salts and organic cation-containing salts.

7. The method of claim 1, wherein the graphitic negative electrode comprises highly ordered pyrolytic graphite.

8. The method of claim 1, wherein the method is a method for the production in an electrochemical cell of graphene and/or graphite nanoplatelet structures having a thickness of less than 100 nm.

9. The method of claim 1, wherein the method is a method for the production in an electrochemical cell of graphane.

10. The method of claim 1, wherein temperature of the electrochemical cell does not exceed 60° C.

11. The method of claim 1, wherein the method includes the step of functionalizing the graphene or graphite nanoplatelet structures such that material produced from the method contains one or more functionalized regions such that the material contains more than 5 at % total non-carbon elements based on total number of atoms in the material.

12. The method of claim 1, wherein a material comprising a surface is produced from the method and wherein the material contains on at least some of its surface a metal-containing material, wherein the metal is selected from Fe and Sn.

13. The method of claim 1, further comprising the step of isolating the one or more of graphene, graphite nanoplatelet structures, and graphane.

14. The method of claim 1, wherein temperature of the electrochemical cell does not exceed 40° C.

15. The method of claim 1, wherein the method includes the step of functionalizing the graphene or graphite nanoplatelet structures such that material produced from the method contains one or more functionalized regions such that the material contains more than 10 at % total non-carbon elements based on total number of atoms in the material.

16. The method of claim 1, wherein the method includes the step of functionalizing the graphene or graphite nanoplatelet structures such that material produced from the method contains one or more functionalized regions such that the material contains more than 30 at % total non-carbon elements based on total number of atoms in the material.

17. The method of claim 1, wherein a material comprising a surface is produced from the method and wherein the material contains on at least some of its surface metal-containing nanoparticles, wherein the metal is selected from Fe and Sn.

18. The method of claim 1, wherein a material comprising a surface is produced from the method and wherein the material contains on at least some of its surface metal-containing nanoparticles having a mean average diameter of less than 25 nm, wherein the metal is selected from Fe and Sn.

\* \* \* \* \*